US012648956B2

(12) United States Patent　(10) Patent No.:　US 12,648,956 B2
Quave et al.　(45) Date of Patent:　Jun. 9, 2026

(54) **PENTAGALLOYL GLUCOSE DERIVED FROM *SCHINUS* PLANTS AND METHODS OF USE**

(71) Applicants: Emory University, Atlanta, GA (US);
Georgia Tech Research Corporation, Atlanta, GA (US)

(72) Inventors: Cassandra Quave, Atlanta, GA (US);
Francois Chassagne, Atlanta, GA (US);
Lewis Marquez, Atlanta, GA (US);
Micah Dettweiler, Atlanta, GA (US);
Julia Kubanek, Decatur, GA (US);
Anne M. Sweeney-Jones, Atlanta, GA (US); Bhuwan Khatri Chhetri, Atlanta, GA (US)

(73) Assignees: EMORY UNIVERSITY, Atlanta, GA (US); GEORGIA TECH RESEARCH CORPORATION, Atlanta, GA (US)

( * ) Notice: Subject to any disclaimer, the term of this patent is extended or adjusted under 35 U.S.C. 154(b) by 919 days.

(21) Appl. No.: 17/802,754

(22) PCT Filed: Feb. 26, 2021

(86) PCT No.: PCT/US2021/019873
§ 371 (c)(1),
(2) Date: Aug. 26, 2022

(87) PCT Pub. No.: WO2021/173972
PCT Pub. Date: Sep. 2, 2021

(65) Prior Publication Data
US 2023/0112887 A1　Apr. 13, 2023

Related U.S. Application Data

(60) Provisional application No. 62/982,897, filed on Feb. 28, 2020.

(51) Int. Cl.
*A61K 31/7024*　(2006.01)
*A61K 45/06*　(2006.01)
*A61P 31/04*　(2006.01)
*A61P 31/10*　(2006.01)

(52) U.S. Cl.
CPC .......... *A61K 31/7024* (2013.01); *A61K 45/06* (2013.01); *A61P 31/04* (2018.01); *A61P 31/10* (2018.01)

(58) Field of Classification Search
CPC .......... A61P 31/04; A61P 31/10; A61K 36/22; A61K 31/7024
See application file for complete search history.

(56) References Cited

U.S. PATENT DOCUMENTS

| | | | |
|---|---|---|---|
| 5,159,069 A | 10/1992 | Hirayama | |
| 8,722,040 B2 | 5/2014 | Huang et al. | |
| 8,900,625 B2 | 12/2014 | Damaj | |
| 9,120,744 B2 | 9/2015 | Lawrence | |
| 10,675,315 B2 | 6/2020 | Quave | |
| 2011/0027399 A1 | 2/2011 | Shimamoto | |
| 2012/0321566 A1* | 12/2012 | Liu | A61P 17/02 |
| | | | 514/35 |
| 2012/0328593 A1 | 12/2012 | Huang et al. | |
| 2017/0112877 A1 | 4/2017 | Huang | |
| 2019/0169623 A1 | 6/2019 | Starzl | |
| 2019/0192581 A1 | 6/2019 | Von Maltzahn | |

FOREIGN PATENT DOCUMENTS

| | | |
|---|---|---|
| EP | 0374888 A2 | 6/1990 |
| EP | 1886662 | 4/2014 |
| WO | 2012178127 | 12/2012 |
| WO | 2020061553 | 3/2023 |

OTHER PUBLICATIONS

Stewart, P. S., et al. Lancet 2001; 358: 135-38. (Year: 2001).*
Miyasaki, Y., et al. PLoS One. 2013, 8(4): e61594. (Year: 2013).*
Zhou, G., et al. Can. J. Microbiol. 2014, 60: 5-14. (Year: 2014).*
Aldulaimi, O. A. Pharmacognosy Reviews. 2017, 11(22), 2017 (Year: 2017).*
Duarte de Freitas, A. L., et al. Journal of Ethnopharmacology. 216, 2018, 184-190. (Year: 2018).*
Intra, J., et al. Antibiotics 2023, 12, 775. (Year: 2023).*
Penta-O-galloyl-beta-D-glucose. Compound Summary. PubChem. Web. (Year: 2025).*
Baylor College of Medicine. Department of Molecular Virology and Microbiology. Methicillin-Resistant *Staphylococcus aureus* (MRSA). Web. 2025 (Year: 2025).*
Karah, N., et al. FEMS Microbes. 2023, 4, 1-4. (Year: 2023).*
Behrendt et al. Pentagalloylglucose, a highly bioavailable polyphenolic compound present in Cortex moutan, efficiently blocks hepatitis C virus entry, Antiviral Research 147 (2017) 19-28.
Brandao et al. Brazilian medicinal plants described by 19th century European naturalists and in the Official Pharmacopoeia, Journal of Ethnopharmacology 120 (2008) 141-148.
Cannell et al. Purification and characterization of pentagalloylglucose, an a-glucosidase inhibitor/antibiotic from the freshwater green alga *Spirogyra varians*, Biochem. J. (1988) 255, 937-941.
Cho et al. Isolation and identification of pentagalloylglucose with broad-spectrum antibacterial activity from Rhus trichocarpa Miquel, Food Chemistry 123 (2010) 501-506.

(Continued)

*Primary Examiner* — Andrea Olson
*Assistant Examiner* — Samuel L Galster
(74) *Attorney, Agent, or Firm* — Kilpatrick Townsend & Stockton LLP

(57)　　ABSTRACT

This disclosure relates to pentagalloyl glucose compositions and uses in managing microbial infections and compositions related thereto. In certain embodiments, this disclosure relates to compositions of pentagalloyl glucose. In certain embodiments, this disclosure relates to methods of treating or preventing a microbial infection, e.g., an antimicrobial resistant microbial infection, comprising administering to a subject in need thereof an effective amount of pentagalloyl glucose or salt thereof. In certain embodiments, the microbe is bacteria or fungi resistant to one or more antibiotic agents or antifungal agents.

13 Claims, 6 Drawing Sheets

(56) References Cited

OTHER PUBLICATIONS

Cowan et al. Plant Products as Antimicrobial Agents, Clinical Microbiology Reviews, 1999, p. 564-582.

Dettweller et al. Pentagalloyl glucose from Schinus terebinthifolia inhibits growth of carbapenem-resistant Acinetobacter baumannii, Scientific Reports (2020) 10:15340, 12 pages.

El-Massry et al. Chemical Compositions and Antioxidant/ Antimicrobial Activities of Various Samples Prepared from Schinus terebinthifolius Leaves Cultivated in Egypt, J. Agric. Food Chem. 2009, 57, 5265-5270.

Feldman et al. In Vitro and In Vivo Inhibition of LPS-Stimulated Tumor Necrosis Factor-a Secretion by the Gallotannin B-D-Pentagalloylglucose, Bioorganic & Medicinal Chemistry Letters 11 (2001) 1813-1815.

Jiamboonsri et al. Factors Influencing Oral Bioavailability of Thai Mango Seed Kernel Extract and Its Key Phenolic Principles, Molecules, 2015, 20, 21254-21273.

Li et al. Anti-Influenza Virus Activity and Constituents Characterization of Paeonia delavayi Extracts, Molecules 2016, 21, 1133.

Lin et al. Inhibitory Effects of 1,2,3,4,6-Penta-O-Galloyl-B-D-Glucopyranose on Biofilm Formation by *Staphylococcus aureus*, Antimicrobial Agents and Chemotherapy, 2011, 1021-1027.

Morton, Brazilian Pepper—Its Impact on People, Animals, and the Environment, Economic Botany, 1978, 32(4):353-359.

Moura-Costa et al. Antimicrobial activity of plants used as medicinals on an indigenous reserve in Rio das Cobras, Parana, Brazil, Journal of Ethnopharmacology 143 (2012) 631-638.

Patnaik et al. Pentagalloyl Glucose and Its Functional Role in Vascular Health: Biomechanics and Drug-Delivery Characteristics, Ann Biomed Eng. 2019, 47(1): 39-59.

Zhao et al. Isolation of Antifungal Compound from Paeonia Suffruticosa and Its Antifungal Mechanism, Chin J Integr Med, 2015, 21(3):211-216.

"Extended European Search Report", issued by the European Patent Office for application No. EP21761821.4 on Dec. 15, 2023, 10 pages.

Silva, et al., "Exploring the Phytochemical Profile of *Cytinus hypocistis* (L.) L. As a Source of Health-promoting Biomolecules Behind Its in Vitro Bioactive and Enzyme Inhibitory Properties", Food and Chemical Toxicology, vol. 136, Dec. 21, 2019, 9 pages.

Juven BJ, et al., "Antibacterial Effects of Hydrogen Peroxide and Methods for Its Detection and Quantitation" J Food Prot. Nov. 1996;59(11): pp. 1233-1241.

* cited by examiner

FIG. 2A                                    FIG. 2B

PENTAGALLOYL GLUCOSE DERIVED FROM *SCHINUS* PLANTS AND METHODS OF USE

CROSS-REFERENCE TO RELATED APPLICATIONS

This application is the National Stage of International Application No. PCT/US2021/019873 filed Feb. 26, 2021, which claims the benefit of U.S. Provisional Application No. 62/982,897 filed Feb. 28, 2020. The entirety of each of these applications is hereby incorporated by reference for all purposes.

STATEMENT REGARDING FEDERALLY FUNDED RESEARCH

This invention was made with government support under AI136563 awarded by the National Institutes of Health. The government has certain rights in the invention.

BACKGROUND

Since the widespread introduction of antibiotics in the 1940s, the same storyline has repeated itself over and over again: new antibiotic is introduced and then resistant variants emerge and quickly spread, effectively limiting the utility and lifespan of the drug. Improved therapies are needed.

*Schinus terebinthifolia* Raddi (synonym: *Schinus terebinthifolius*) is a flowering plant in the family Anacardiaceae, which can be found in Brazil, the Caribbean and across the southern United States. El-Massry et al. report chemical compositions and antioxidant/antimicrobial activities of various samples prepared from *Schinus terebinthifolia* leaves cultivated in Egypt. J Agric Food Chem, 2009, 57:5265-5270. Moura-Costa et al. report antimicrobial activity of plants used as medicinals on an indigenous reserve in Rio das Cobras, Parana, Brazil. J Ethnopharmacol, 2012, 143:631-638.

Cho et al. report the isolation and identification of pentagalloyl glucose with broad-spectrum antibacterial activity from *Rhus trichocarpa* Miquel. Food Chem, 2010, 123, 501-506.

References cited herein are not an admission of prior art.

SUMMARY

This disclosure relates to pentagalloyl glucose compositions and uses in managing microbial infections and compositions related thereto. In certain embodiments, this disclosure relates to compositions of pentagalloyl glucose derived from *Schinus* plants. In certain embodiments, this disclosure relates to methods of treating or preventing a microbial infection, e.g., an antimicrobial resistant microbial infection, comprising administering to a subject in need thereof an effective amount of pentagalloyl glucose or salt thereof. In certain embodiments, the microbe is bacteria or fungi resistant to one or more antibiotic agents or antifungal agents.

In certain embodiments, the bacteria are an *Acinetobacter* species. In certain embodiments, the fungi are a *Candida* species.

In certain embodiments, the bacteria are resistant to one or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are an *Enterococcus* species. In certain embodiments, the bacteria are resistant to gentamicin and/or vancomycin.

In certain embodiments, the bacteria are a *Staphylococcus* species. In certain embodiments, the bacteria are resistant to oxacillin.

In certain embodiments, the bacteria are a *Klebsiella* species. In certain embodiments, the bacteria are resistant to one or more antibiotic agents selected from ampicillin, sulbactam, cefepime, ceftazidime, ciprofloxacin, imipenem, meropenem, and combinations thereof.

In certain embodiments, the bacteria are a *Pseudomonas* species. In certain embodiments, the bacteria are resistant to one or more antibiotic agents selected from ampicillin, cefepime, ceftazidime, ciprofloxacin, gentamicin, imipenem, meropenem, tobramycin, and combinations thereof.

In certain embodiments, the bacteria are an *Enterobacter* species. In certain embodiments, the bacteria are resistant to one or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to a carbapenem antibiotic. In certain embodiments, the carbapenem is selected from imipenem, meropenem, ertapenem, doripenem, panipenem, biapenem, and tebipenem.

In certain embodiments, the bacteria are resistant to a penicillin. In certain embodiments, the penicillin is selected from cloxacillin, dicloxacillin, flucloxacillin, methicillin, nafcillin, oxacillin, benzylpenicillin, and phenoxymethylpenicillin.

In certain embodiments, the bacteria are *Acinetobacter baumannii* that is resistant to a carbapenem antibiotic.

In certain embodiments, the administering is contacting the skin, open wound, or wound of the skin of the subject with a pharmaceutical formulation comprising pentagalloyl glucose.

In certain embodiments, this disclosure relates to methods of treating or preventing a fungal infection comprising administering to a subject in need thereof an effective amount of pentagalloyl glucose or salt thereof, wherein the fungi are resistant to one or more antibiotic agents.

In certain embodiments, the fungi are a *Candida* species. In certain embodiments, the fungi are resistant to one or more antifungal agents selected from anidulafungin, caspofungin, fluconazole, micafungin, voriconazole, and combinations thereof.

In certain embodiments, this disclosure relates to pharmaceutical formulation comprising pentagalloyl glucose or salt thereof. In certain embodiments, the pharmaceutical formulation is in the form of a lotion, gel, or hydrogel. In certain embodiments, the pharmaceutical formulation comprises another antibiotic agent.

BRIEF DESCRIPTION OF THE DRAWINGS

FIG. 2A shows data on daily serial passaging of *A. baumannii* AB5075 with PGG and tetracycline, showing change in dose-response curves of PGG. Base MICs are 256 µg/mL for PGG and 4 µg/mL for tetracycline.

FIG. 2B shows data using tetracycline.

DETAILED DISCUSSION

Figure 1:
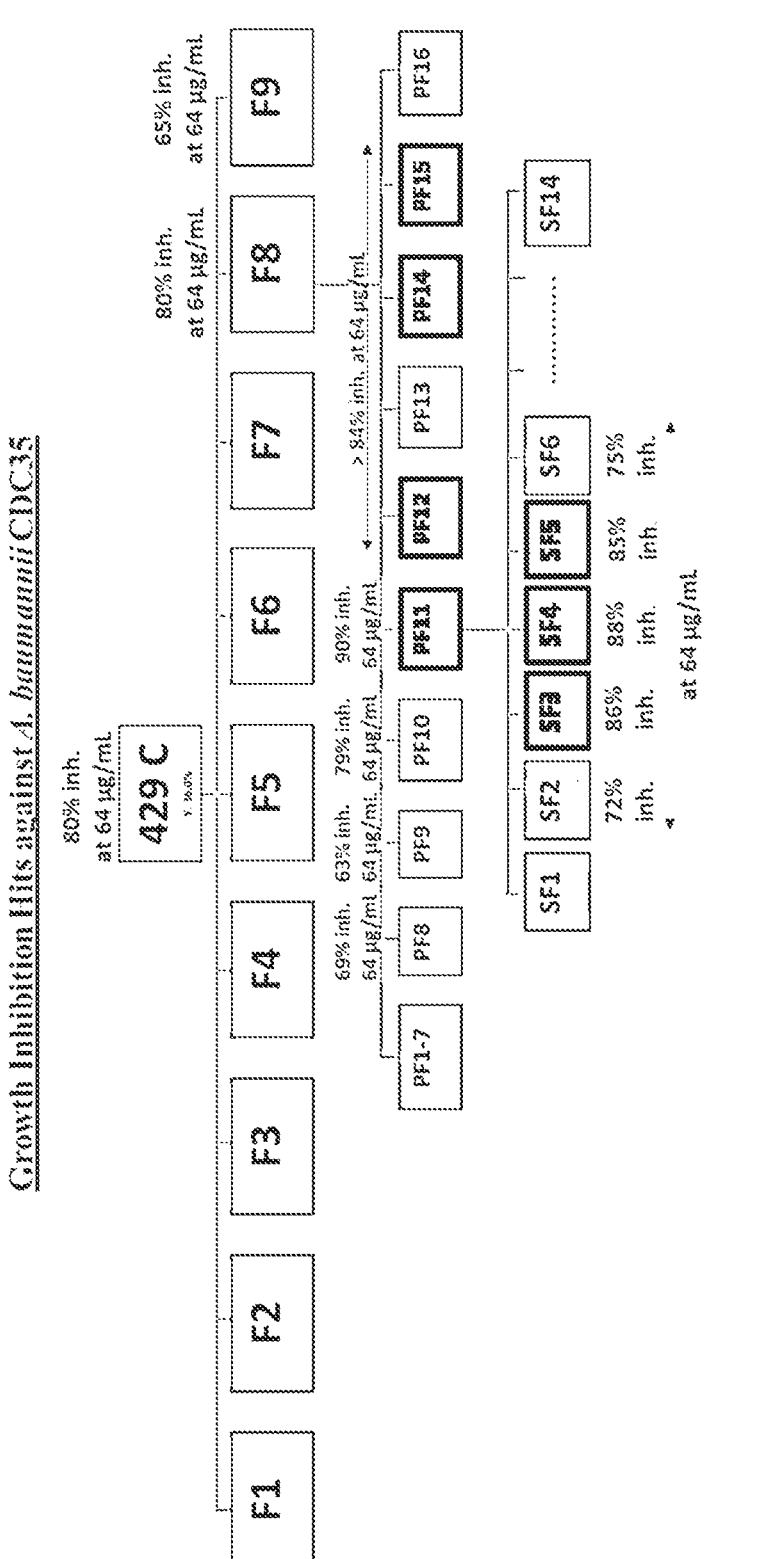
FIG. 1 illustrates bioassay-guided fractionation of extract 429 from *Schinus terebinthifolia* leaves using growth inhibition of CRAB.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent. For example, "an antibiotic" refers to one or a combination of antibiotics.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. patent law in that they are inclusive or open-ended and do not exclude additional, unrecited elements or method steps. "Consisting essentially of" or "consists essentially" or the like, when applied to methods and compositions encompassed by the present disclosure refers to compositions like those disclosed herein that exclude certain prior art elements to provide an inventive feature of a claim, but which may contain additional composition components or method steps composition components or method steps, etc., that do not materially affect the basic and novel characteristic(s) of the compositions or methods, compared to those of the corresponding compositions or methods disclosed herein.

As used herein, the term "combination with" when used to describe administration with an additional treatment means that the agent may be administered prior to, together with, or after the additional treatment, or a combination thereof.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

Microbial Resistance, Heteroresistance, and Susceptibility

A microbial isolate from a clinical sample can be tested for anti-microbial resistance in vitro prior to administering anti-microbial agent(s) to a patient using conventional tests, e.g., bacterial susceptibility tests, such as an ETEST® and broth microdilution assays. Antibacterial susceptibility tests are typically performed in suspension assays (e.g., broth microdilution assay) or in agar plate assays (e.g., disk diffusion assay). The ETEST® or Epsilometer test is a strip containing an antibiotic gradient used to determine whether or not a specific bacterial strain is susceptible to the action of a specific antibiotic. When the ETEST® strip is placed on an agar surface, the antibiotic gradient on the strip is transferred to the agar creating an imprint of the gradient on the strip in the agar. The bacterial growth becomes visible after incubation and an inhibition ellipse centered along the strip can be seen. The MIC (Minimum Inhibitory Concentration) value is read from the scale where the ellipse edge intersects the strip.

As used herein, the term "resistance" to an antimicrobial agent, e.g., antibiotic or antifungal or combinations thereof, refers to contacting the bacterial culture with the agent(s) and observing that the agent(s) do not kill or do not prevent growth of an observable amount of the microbes. The term is intended to include both resistant and intermediate resistant strains sometimes referred to as heteroresistant strains, see PCT International Patent Application Number WO2020061553. In certain embodiments, a resistant microbe may be resistant without heteroresistance. In certain embodiments, a resistant microbe may be resistant with heteroresistance. "Heteroresistance" refers to testing with the anti-microbial agent(s) and observing that the agent(s) kills or prevents growth of an observable portion, but not all, of the microbes. Sometimes vast majority or low concentration of the microbes, e.g., bacteria or fungi, are resistant to the agent. Some of the individual cells would be susceptible. Nevertheless, the resistant ones grow out if treating with only that specific antibiotic or combination over time. Thus, the microbial culture harbors a subpopulation of cells resistant to the agent(s).

Methods of Use

In certain embodiments, this disclosure relates to methods of treating or preventing a microbial infection, e.g., an antimicrobial resistant microbial infection, comprising administering to a subject in need thereof an effective amount of pentagalloyl glucose or salt thereof. In certain embodiments, the microbe is bacteria or fungi resistant to one or more antibiotic agents or antifungal agents.

In certain embodiments, the bacteria are an *Acinetobacter* species. In certain embodiments, the fungi are a *Candida* species.

In certain embodiments, the bacteria are resistant to one or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are resistant to two or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are resistant to three or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are resistant to four or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are resistant to five or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are resistant to six or more antibiotic agents selected from amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

In certain embodiments, the bacteria are an *Enterococcus* species. In certain embodiments, the bacteria are resistant to gentamicin and/or vancomycin.

In certain embodiments, the bacteria are a *Staphylococcus* species. In certain embodiments, the bacteria are resistant to oxacillin.

In certain embodiments, the bacteria are a *Klebsiella* species. In certain embodiments, the bacteria are resistant to one or more antibiotic agents selected from ampicillin, sulbactam, cefepime, ceftazidime, ciprofloxacin, imipenem, meropenem and combinations thereof.

In certain embodiments, the bacteria are resistant to two or more antibiotic agents selected from ampicillin, sulbactam, cefepime, ceftazidime, ciprofloxacin, imipenem, meropenem and combinations thereof.

In certain embodiments, the bacteria are resistant to three or more antibiotic agents selected from ampicillin, sulbactam, cefepime, ceftazidime, ciprofloxacin, imipenem, meropenem and combinations thereof.

In certain embodiments, the bacteria are resistant to four or more antibiotic agents selected from ampicillin, sulbactam, cefepime, ceftazidime, ciprofloxacin, imipenem, meropenem and combinations thereof.

In certain embodiments, the bacteria are resistant to five or more antibiotic agents selected from ampicillin, sulbactam, cefepime, ceftazidime, ciprofloxacin, imipenem, meropenem and combinations thereof.

In certain embodiments, the bacteria are a *Pseudomonas* species. In certain embodiments, the bacteria are resistant to one or more antibiotic agents selected from ampicillin, cefepime, ceftazidime, ciprofloxacin, gentamicin, imipenem, meropenem, tobramycin, and combinations thereof.

In certain embodiments, the bacteria are resistant to two or more antibiotic agents selected from ampicillin, cefepime, ceftazidime, ciprofloxacin, gentamicin, imipenem, meropenem, tobramycin, and combinations thereof.

In certain embodiments, the bacteria are resistant to three or more antibiotic agents selected from ampicillin, cefepime, ceftazidime, ciprofloxacin, gentamicin, imipenem, meropenem, tobramycin, and combinations thereof.

In certain embodiments, the bacteria are resistant to four or more antibiotic agents selected from ampicillin, cefepime, ceftazidime, ciprofloxacin, gentamicin, imipenem, meropenem, tobramycin, and combinations thereof.

In certain embodiments, the bacteria are resistant to five or more antibiotic agents selected from ampicillin, cefepime, ceftazidime, ciprofloxacin, gentamicin, imipenem, meropenem, tobramycin, and combinations thereof.

In certain embodiments, the bacteria are an *Enterobacter* species. In certain embodiments, the bacteria are resistant to one or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to two or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to three or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to four or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to five or more antibiotic agents selected from ampicillin, sulbactam, cefepime, ceftazidime, ciprofloxacin, gentamicin, imipenem, meropenem, tobramycin, and combinations thereof.

In certain embodiments, the bacteria are resistant to a carbapenem antibiotic. In certain embodiments, the carbapenem is selected from imipenem, meropenem, ertapenem, doripenem, panipenem, biapenem, and tebipenem.

In certain embodiments, the bacteria are resistant to a penicillin. In certain embodiments, the penicillin is selected from cloxacillin, dicloxacillin, flucloxacillin, methicillin, nafcillin, oxacillin, benzylpenicillin, and phenoxymethylpenicillin.

In certain embodiments, the bacteria are *Acinetobacter baumannii* that is resistant to a carbapenem antibiotic, e.g., doripenem, ertapenem, imipenem, meropenem, or others.

In certain embodiments, the administering is contacting the skin, open wound, or wound of the skin of the subject with a pharmaceutical formulation comprising pentagalloyl glucose.

In certain embodiments, this disclosure relates to methods of treating or preventing a fungal infection comprising administering to a subject in need thereof an effective amount of pentagalloyl glucose or salt thereof, wherein the fungi are resistant to one or more antibiotic agents.

In certain embodiments, the fungi are a *Candida* species. In certain embodiments, the fungi are resistant to one or more antifungal agents selected from anidulafungin, caspofungin, fluconazole, micafungin, voriconazole, and combinations thereof.

In certain embodiments, the fungi are resistant to two or more antifungal agents selected from anidulafungin, caspofungin, fluconazole, micafungin, voriconazole, and combinations thereof.

In certain embodiments, the fungi are resistant to three or more antifungal agents selected from anidulafungin, caspofungin, fluconazole, micafungin, voriconazole, and combinations thereof.

In certain embodiments, the fungi are resistant to four or more antifungal agents selected from anidulafungin, caspofungin, fluconazole, micafungin, voriconazole, and combinations thereof.

In certain embodiments, this disclosure relates to pharmaceutical formulation comprising pentagalloyl glucose or salt thereof. In certain embodiments, the pharmaceutical formulation is in the form of a lotion, gel, or hydrogel. In certain embodiments, the pharmaceutical formulation comprises another antibiotic agent.

In certain embodiments, this disclosure relates to extracts from the cashew family of plants (Anacardiaceae) and compositions comprising one or more compounds contained therein and related uses reported herein. In certain embodiments, the extracts are derived from a *Rhus* or *Schinus* plant such as *Schinus terebinthifolia.*

In certain embodiments, the disclosure relates to extracts comprising a derived mixture of compounds from a *Schinus* plant wherein the extracting process comprises one or more of the following steps of: mixing a fruit with an alcohol, e.g., ethanol, methanol, or aqueous mixtures thereof (ethanol: water or methanol:water, 50-95% alcohol, 80% methanol) under conditions such that fruit compounds dissolves in the methanol and removing the methanol providing a methanol derived mixture of compounds; partitioning the methanol derived mixture of compounds between hexane and water providing a water derived mixture of compounds; partitioning the water derived mixture of compounds between ethyl acetate and water providing a second water derived mixture of compounds; partitioning the second water derived mixture of compounds by mixing the second water derived mixture of compounds with n-butanol under conditions such that fruit compounds dissolve in the n-butanol and removing the n-butanol providing an n-butanol derived mixture of compounds; and purifying the n-butanol derived mixture of compounds by liquid chromatography.

In certain embodiments, this disclosure relates to methods of treating or preventing microbial infections, bacterial infections, fungal infections, wounds, skin abrasions, or acne comprising administering to a subject in need thereof or contacting the skin or wound of a subject in need thereof with a formula comprising pentagalloyl glucose. In certain embodiments, the formula is administered in combination with another antimicrobial agent, antibiotic, or antifungal.

In certain embodiments, this disclosure relates to methods of treating or preventing a toxin-mediated bacterial infection comprising administering an effective amount of an *Schinus* extract or compounds contained therein to a subject in need thereof, including a subject at risk of, exhibiting symptoms of, or diagnosed with a staphylococcal scalded skin syndrome (esp. in neonates), abscesses, necrotizing fasciitis, sepsis, or atopic dermatitis (eczema).

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, staphylococcal food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates the use of pentagalloyl glucose in a tampon for the treatment or prevention of toxic shock syndrome.

In certain embodiments, the disclosure relates to a pharmaceutical or cosmetic formulation comprising pentagalloyl glucose and a pharmaceutically acceptable excipient or cosmetically acceptable excipient.

In certain embodiments, the disclosure relates to a liquid or gel formulation optionally further comprising an antimicrobial agent, antibacterial agent, or antifungal agent and a topical steroid, an anti-inflammatory agent, a promoter of skin barrier function, a skin moisturizer, or combinations thereof.

In certain embodiments the antibacterial agent is daptomycin, linezolid, vancomycin, nafcillin, cefazolin, dicloxacillin, clindamycin, rifampin, sulfamethoxazole-trimethoprim (Bactrim), or botanical antibacterial agents, e.g., *Melaleuca alternfolia* (tea tree oil).

In certain embodiments, the compound is in the form of an aqueous solution further comprising a buffering agent, oil, phosphate buffer, sodium or potassium salt, a saccharide, polysaccharide, or solubilizing agent.

Uses as an injectable product (for intravenous, intramuscular, subcutaneous, intradermal injections, intraperitoneal, or other administration) are contemplated. In certain embodiments, the disclosure relates to a pharmaceutical injectable formulation comprising pentagalloyl glucose and a pharmaceutically acceptable excipient. In certain embodiments, the disclosure relates to an injectable formulation optionally further comprising an antibacterial agent, a topical steroid, an anti-inflammatory agent, or combinations thereof. In certain embodiments the antibacterial agent is daptomycin, linezolid, vancomycin, nafcillin, cefazolin, dicloxacillin, clindamycin, rifampin, sulfamethoxazole-trimethoprim (Bactrim), or botanical antibacterial agents, e.g., *Melaleuca alternfolia* (tea tree oil).

In certain embodiments, the pentagalloyl glucose is administered by inhalation through the lungs. In certain embodiments, this disclosure contemplates pharmaceutical compositions of pentagalloyl glucose for use in an inhalant therapy, e.g., applications in breathing treatments for pneumonia caused by any of these pathogens for patients with ventilator associated pneumonia (VAP).

In certain embodiments, the pharmaceutical composition comprises pentagalloyl glucose and a propellant. In certain embodiments, an aerosolizing propellant is compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising pentagalloyl glucose. In certain embodiments, the container is a manual pump spray, inhaler, meter-dosed inhaler, dry powder inhaler, nebulizer, vibrating mesh nebulizer, jet nebulizer, or ultrasonic wave nebulizer.

In certain embodiments, the disclosure relates to a pharmaceutical composition comprising pentagalloyl glucose formulated with an enteric coating.

In certain embodiments, the disclosure relates to a solid or liquid soap or lotion comprising pentagalloyl glucose and a fatty acid.

In certain embodiments, the disclosure relates to a medical device comprising a coating comprising pentagalloyl glucose.

In certain embodiments, the disclosure relates to a tampon or tampon fibers comprising pentagalloyl glucose and an absorbent material.

In certain embodiments, the disclosure relates to a wound dressing, a medicated bandage, or wound rinse comprising pentagalloyl glucose wherein the wound dressing comprises an absorbent pad and optionally an adhesive. In certain embodiments, a bandage impregnated with pentagalloyl glucose is a medical device.

In certain embodiments, the disclosure relates to disinfectant sprays or wipes formulation for surfaces and fomites, comprising pentagalloyl glucose wherein the spray or wipe optionally comprises chlorine-based disinfectants.

In certain embodiment, this disclosure contemplates that compounds disclosed herein are used in a substantially purified form. For example, prior to addition to a pharmaceutical formulation the compounds may be purified to contain less than 50%, 40%, 30%, 20%, 10%, or 5%, by weight impurities or derivatives of the compound.

In certain embodiments, this disclosure relates to methods of treating or preventing bacterial infections comprising administering or contacting a formula comprising pentagalloyl glucose to a subject in need thereof. In certain embodiments, the formula is administered in combination with another antimicrobial, antibiotic, or antifungal agent.

In further embodiments, the subject is co-administered with an antibiotic selected from the group comprising of sulfonamides, diaminopyrimidines, quinolones, beta-lactam antibiotics, cephalosporins, tetracyclines, nitrobenzene derivatives, aminoglycosides, macrolide antibiotics, polypeptide antibiotics, nitrofuran derivatives, nitroimidazoles, nicotinic acid derivatives, polyene antibiotics, imidazole derivatives or glycopeptide, cyclic lipopeptides, glycylcyclines and oxazolidinones. In further embodiments, these antibiotics include but are not limited to sulfadiazine, sulfones—[dapsone (DDS) and para-aminosalicylic acid (PAS)], sulfanilamide, sulfamethizole, sulfamethoxazole, sulfapyridine, trimethoprim, pyrimethamine, nalidixic acids, norfloxacin, ciprofloxacin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefalonium, cefalotin, cefapirin, cefatrizine, cefazedone, cefazolin, cefradine, cefroxadine, ceftezole, cefaclor, cefonicid, ceforanide, cefprozil, cefuroxime, cefuzonam, cefmetazole, cefoxitin, cefcapene, cefdaloxime, cefdinir, cefditoren, cefetamet, cefixime, cefmenoxime, cefodizime, cefoperazone, cefotaxime, cefotiam, cefpiramide, cefpodoxime, cefteram, ceftibuten, ceftiofur, ceftizoxime, ceftriaxone, cefoperazone, ceftazidime, cefepime), carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, furazolidone, metronidazole, tinidazole, isoniazid, pyrazinamide, ethionamide, nystatin, amphotericin-B, hamycin, miconazole, clotrimazole, ketoconazole, fluconazole, lincomycin, clindamycin, spectinomycin, fosfomycin, loracarbef, polymyxin B, polymyxin B Sulfate, ramoplanin, teicoplanin, vancomycin, and/or nitrofurantoin.

In certain embodiments, this disclosure relates to methods of treating or preventing a toxin-mediated infection comprising administering an effective amount of pentagalloyl glucose to a subject in need thereof, including a subject at risk of, exhibiting symptoms of, or diagnosed with a staphylococcal scalded skin syndrome (esp. in neonates), abscesses, necrotizing fasciitis, sepsis, atopic dermatitis (eczema) and more.

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, staphylococcal food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates methods of preventing microbial, bacterial, or fungal infections by applying pentagalloyl glucose in a tampon for prevention against adverse effects associated with vaginal area infections and possibly bladder infections, e.g., toxic shock syndrome. As used herein a "tampon" refers to device containing an absorbent material, configured to be inserted into a vagina to absorb menstrual flow and typically expand during use, typically in the shape of a cylinder. Tampons may expand axially (increase in length), while digital tampons will expand radially (increase in diameter). Most tampons have a cord or string for removal. Typical tampon materials include cloth, fibers, cotton, or rayon, or a blend of rayon and cotton.

Bacterial toxins may cause toxic shock syndrome (TSS). Enterotoxin type B or TSST-1 of *Staphylococcus aureus* are believed to cause TSS. Streptococcal TSS is sometimes referred to as toxic shock-like syndrome (TSLS) or streptococcal toxic shock syndrome (STSS). CDC criteria for diagnosing staphylococcal toxic shock syndrome is based on 1) a body temperature of greater than 38.9° C. (102° F.) 2) a Systolic blood pressure of greater than 90 mmHg 3) diffuse macular erythroderma 4) desquamation (especially of the palms and soles) 1-2 weeks after onset 5) involvement of three or more organ systems: gastrointestinal (vomiting, diarrhea), muscular: severe myalgia or creatine phosphokinase level at least twice the upper limit of normal for laboratory, mucous membrane hyperemia (vaginal, oral, conjunctival), kidney failure (serum creatinine>2 times normal), liver inflammation (bilirubin, AST, or ALT>2 times normal), low platelet count (platelet count <100,000/mm³), central nervous system involvement (confusion without any focal neurological findings) and 6) negative results of: blood, throat, and CSF cultures for other bacteria (besides *S. aureus*) negative serology for *Rickettsia* infection, leptospirosis, and measles. Cases are classified as probable if five of the six criteria above are met.

In certain embodiments, the disclosure contemplates methods of preventing general transmission of microbes, bacteria, or fungi through use of pentagalloyl glucose as a general agent formulated into a spray or wipe product, paper or fiber-based cloth. For example, one can use such a product to treat athletic equipment (football pads, bench presses, gym surfaces), where invasive toxin mediated *staphylococcus* often lurks and causes infections in healthy people through toxin production.

In certain embodiments, the disclosure relates to methods of treating acne comprising administering an effective amount of a composition comprising pentagalloyl glucose to a subject at risk of, exhibiting symptoms of, or diagnosed with acne, blackheads, papules, pustules, or nodules. In certain embodiments, the subject is in puberty, between 10 and 20 years of age. In certain embodiments, the subject is a female, and the composition is administered within seven days of the beginning of a menstrual cycle. Administration may be by topical application through hand or by spray of a liquid or lotion containing pentagalloyl glucose.

Extracts and Compounds

In certain embodiments, an extract is made by the process of extracting a mixture of compounds from the leaves, roots, bark, stem, fruit, seeds, or branches of a *Rhus* or *Schinus* plant such as *Schinus terebinthifolia*. Other contemplated plants include: *Rhus coriaria, Rhus copallinum,* and Anacardiaceae plants, e.g., mango seeds. Other contemplated plants include: *Schinus andina* and varieties (*andina* and *subtridentata*), *Schinus angustifolia, Schinus antiarthritica, Schinus areira, Schinus bituminosa, Schinus bonplandiana, Schinus brasiliensis, Schinus bumelioides, Schinus canrerae, Schinus chebataroffi, Schinus chichita, Schinus crenata, Schinus dentata, Schinus dependens* and varieties (*alfa, arenicola, brevifolia, crenata, grandifolia, longifolia, obovata, ovata, paraguarensis, parvifolia, patagonica, subintegra, tomentosa*), *Schinus discolor, Schinus diversifolia, Schinus engleri* and varieties (*engleri, uruguayensis*), *Schinus fagara, Schinus fasciculate* and varieties (*arenaria, arenicola, boliviensis, fasciculata*), *Schinus ferox, Schinus gracilipes* and varieties (*gracilipies, pilosus*), *Schinus huigan, Schinus huyngan* and varieties (*heterophyllus, longifolius, obovatus, subtridentata, undulate*), *Schinus indicus, Schinus johnstonii, Schinus latifolius* and varieties (*tomentosus*), *Schinus lentiscifolius* and varieties (*angustifolia, flexuosa, subobtusa*), *Schinus leucocarpus, Schinus limonia, Schinus longifolia* and varieties (*longifolia, paraguarensis*), *Schinus marchandii, Schinus maurioides, Schinus mellisii, Schinus meyeri, Schinus microphylla, Schinus microphyllus, Schinus molle* and varieties (*areira, argentifolius, hassleri, huigan, huyngan, molle, rusbyi*), *Schinus molleoides, Schinus montanus* and varieties (*crenuloides, patagonicus*), *Schinus mucronulatus, Schinus myricoides, Schinus myrtifolia, Schinus occidentalis, Schinus odonellii, Schinus paraguarensis, Schinus patagonicus* and varieties (*crenuloides, patagonicus*), *Schinus pearcei, Schinus pilifera* and varieties (*boliviensis, cabrerae, pilifer*), *Schinus polygama* and varieties (*australis, chubutensis, crenata, fasciculata, heterophylla, ovata, parviflora, patagonica*), *Schinus polygamus,*

*Schinus praecox, Schinus pubescens, Schinus ramboi, Schinus resinosus, Schinus rhoifolia, Schinus roigii, Schinus sinuatus, Schinus spinosus, Schinus tenuifolius, Schinus terebinthifolius* and varieties (*acutifolia, damaziana, glaziovana, pohlianus, raddiana, rhoifolia, selloana, terebinthifolia, ternifolia*), *Schinus terebinthifolius, Schinus ternifolia, Schinus tomentosa, Schinus tragodes, Schinus velutinus, Schinus venturii, Schinus* weinmannfolius and varieties (angustifolius, *dubius, glabrescens, hassleri, intermedius, pauciflorus, paucijuga, pubescens, riedelianus, ridelianus, weinmannfolius*) and hybrids thereof.

In certain embodiments, the extracting process comprises the step of mixing the leaf, stem, bark, or fruit from the plant with a polar solvent, such as a liquid comprising methanol, ethanol, ethyl acetate, n-butanol, acetonitrile, acetone, methylene chloride or chloroform, under conditions such that a mixture of compounds in the fruit dissolves in the solvent. In certain embodiments, the process further comprises the step of removing the solvent by evaporation from the mixture of compounds. In certain embodiments, the process further comprises the step of purifying the mixture of compounds by liquid chromatography through a solid absorbent, e.g., wherein the solid absorbent comprises silica gel or alumina.

In certain embodiments, the disclosure relates to extracts comprising a mixture of compounds from a *Schinus* plant wherein the extracting process comprises the steps of: mixing a part of the plant with methanol under conditions such that compounds dissolves in the methanol and removing the methanol providing a methanol derived mixture of compounds; partitioning the methanol derived mixture of compounds with hexane and water providing a water derived mixture of compounds; partitioning the water derived mixture of compounds with ethyl acetate and water providing a second water derived mixture of compounds; partitioning the second water derived mixture of compounds by mixing the water with n-butanol under conditions such that fruit compounds dissolve in the butanol and removing the n-butanol providing an n-butanol derived mixture of compounds; and purifying the n-butanol derived mixture of compounds by liquid chromatography.

Chromatography refers to the separation of a mixture of compounds dissolved in a fluid called the mobile phase, which carries the compounds through a structure holding another material called the stationary phase. The various compounds or components of the mixture travel at different speeds, causing them to separate. The separation is based on differential partitioning between the mobile and stationary phases. Subtle differences in a partition coefficient of each compound result in differential retention on the stationary phase and thus changing the separation.

In normal-phase chromatography, the stationary phase is polar. In reversed phase, the stationary phase is nonpolar. Typical stationary phases for normal-phase chromatography are silica or organic moieties with cyano and amino functional groups. For reversed phase, alkyl hydrocarbons are the preferred stationary phase. Examples are solid supports containing a surface conjugated with a hydrocarbon chain, e.g., octadecyl (C18), octyl (C8), and butyl (C4).

In normal-phase chromatography, the least polar compounds elute first, and the most polar compounds elute last. The mobile phase typically consists of a nonpolar solvent such as hexane or heptane mixed with a slightly more polar solvent such as isopropanol, ethyl acetate, n-butanol, or chloroform. Retention to the stationary phase decreases as the amount of polar solvent in the mobile phase increases. In reversed phase chromatography, the most polar compounds elute first with the most nonpolar compounds eluting last. The mobile phase is generally a binary mixture of water and a miscible polar organic solvent like methanol, acetonitrile, or tetrahydrofuran.

Pharmaceutical Formulation

In certain embodiments, the disclosure relates to a pharmaceutical formulation comprising pentagalloyl glucose and a pharmaceutically acceptable excipient or additive.

In certain embodiments, the disclosure relates to a lotion, liquid, or gel formulation optionally further comprising an antibiotic agent, antifungal agent, a topical steroid, an anti-inflammatory agent, a promoter of skin barrier function, a skin moisturizer, or combinations thereof.

Examples of antibiotics include but are not limited to pentagalloyl glucose, in addition to amikacin, ampicillin, sulbactam, cefepime, ceftazidime, ciprofloxacin, erythromycin, colistin, gentamicin, imipenem, oxacillin, tetracycline, tigecycline, tobramycin, vancomycin, or combinations thereof.

Other examples include sulfadiazine, sulfones—[dapsone (DDS) and para-aminosalicylic (PAS)], sulfanilamide, sulfamethizole, sulfamethoxazole, sulfapyridine, trimethoprim, pyrimethamine, nalidixic acids, norfloxacin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefalonium, cefalotin, cefapirin, cefatrizine, cefazedone, cefazolin, cefradine, cefroxadine, ceftezole, cefaclor, cefonicid, ceforanide, cefprozil, cefuroxime, cefuzonam, cefmetazole, cefoxitin, cefcapene, cefdaloxime, cefdinir, cefditoren, cefetamet, cefixime, cefmenoxime, cefodizime, cefoperazone, cefotaxime, cefotiam, cefpiramide, cefpodoxime, cefteram, ceftibuten, ceftiofur, ceftizoxime, ceftriaxone, cefoperazone, ceftazidime, cefepime), carbapenems (imipenem, ertapenem, meropenem) monobactams (aztreonam) oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, furazolidone, metronidazole, tinidazole, isoniazid, pyrazinamide, ethionamide, nystatin, amphotericin-B, hamycin, miconazole, clotrimazole, ketoconazole, fluconazole, lincomycin, clindamycin, spectinomycin, fosfomycin, loracarbef, polymyxin B, polymyxin B Sulfate, ramoplanin, teicoplanin, vancomycin, and/or nitrofurantoin.

Examples of antifungal agents include clotrimazole, econazole, miconazole, amphotericin, fluconazole, itraconazole, and ketoconazole naftifine, terbinafine, 5-fluorocytosine, nystatin, amphotericin B, pimaricin, griseofulvin, and amorolfine Examples of steroids include hydrocortisone, hydrocortisone valerate, hydrocortisone 17-butyrate, mometasone, mometasone furoate, halobetasol propionate, desonide, desoximetasone, fluocinolone acetonide, alclometasone dipropionate, flurandrenolide, fluticasone propionate, diflucortolone, diflucortolone valerate, diflorasone diacetate, clobetasol, clobetasone butyrate, clobetasol propionate, betamethasone dipropionate, betamethasone valerate, beclomethasone, budesonide, flunisolide, fluocinonide, triamcinolone, triamcinolone acetonide, methylprednisolone, methylprednisolone aceponate, prednicarbate, prednisolone, and prednisone and alternate salts thereof. Examples of contemplated anti-inflammatory agents are aspirin, celecoxib, diclofenac, diflunisal, etodolac, ibuprofen, indomethacin, ketoprofen, naproxen, oxaprozin, and piroxicam.

In certain embodiments, the disclosure relates to a pharmaceutical composition comprising pentagalloyl glucose formulated with an enteric coating. In certain embodiments, the disclosure relates to a pharmaceutical formulation of pentagalloyl glucose which protect the compositions from the acidity and enzymatic action of gastric secretions. In certain embodiments, the pharmaceutical formulations contain pentagalloyl glucose in a composition with an enteric coating along with another pharmaceutically acceptable vehicle. In certain embodiments, compositions comprising pentagalloyl glucose may be directly compressible without excipients, into a tablet of pharmaceutically acceptable hardness, e.g., compressed into a tablet, optionally with a lubricant, such as but not limited to magnesium stearate, and enteric coated. In another embodiment, the pharmaceutical compositions containing pentagalloyl glucose alternatively include one or more substances that either neutralize stomach acid and/or enzymes or are active to prevent secretion of stomach acid.

The pharmaceutical composition can be formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be formulated for oral administration as a solution or suspension in an aqueous liquid, as a liquid incorporated into a gel capsule or as any other convenient formulation for administration, or for rectal administration, as a suppository, enema or other convenient form.

In certain embodiments, this disclosure contemplates a pharmaceutical formulation in the form of a soft or lubricated tablet to place inside the vagina.

The injectable solutions or suspensions may be formulated according to known art, using suitable non-toxic, parenterally-acceptable diluents or solvents, such as mannitol, 1,3-butanediol, water, isotonic sodium chloride solution, or suitable dispersing or wetting and suspending agents, such as sterile, bland, fixed oils, including synthetic mono- or diglycerides, and fatty acids, including oleic acid.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic, or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions. The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM $MgCl_2$, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The pharmaceutical formulation can also include any type of pharmaceutically acceptable excipients, additives, or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropyl methylcellulose may be added to the composition comprising pentagalloyl glucose to increase the bulk of the composition. Also, binders, such as but not limited to, starch, gelatin, sucrose, glucose, dextrose, molasses, lactose, acacia gum, sodium alginate, carboxymethylcellulose, methylcellulose, polyvinylpyrrolidone, starch, polyethylene glycol, ethylcellulose, and waxes, may be added to the formulation to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide or talc may be added to improve the flow characteristics of a powdered formulation. Finally, disintegrants, such as but not limited to, starches, clays, celluloses, algins, gums, crosslinked polymers (e.g., croscarmellose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the intestine.

In certain embodiments, the formulation contains a directly compressible composition comprising pentagalloyl glucose but no excipients, additives, or vehicles other than an enteric coating; however, the formulation may contain a lubricant, such as but not limited to, magnesium stearate. Preferably, the directly compressed formulation is formulated as a tablet of pharmaceutically acceptable hardness (greater than 6 kp, preferably 8-14 kp, and more preferably 10-13 kp).

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinyl acetate phthalate (PVAP), hydroxypropyl methylcellulose phthalate (grades HP-50 and HP-55), ethylcellulose, fats, butyl stearate, and methacrylic acid-methacrylic acid ester copolymers with acid ionizable groups.

Application of the enteric coating to composition can be accomplished by any method known in the art for applying enteric coatings. For example, but not by way of limitation, the enteric polymers can be applied using organic solvent-based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethylene glycol, tributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

Cosmetic Formulations and Personal Care Products

In certain embodiments, the disclosure relates to a cosmetic formulation comprising pentagalloyl glucose and cosmetically acceptable excipient or additive. In certain embodiments, the disclosure relates to a solid or liquid soap or lotion comprising pentagalloyl glucose and a fatty acid.

In certain embodiments, additives can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In certain embodiments, additives are selected from the group consisting of surfactants, emulsifiers, fats, waxes, stabilizers, deodorants, antiperspirants, antidandruff agents, and perfume oils.

As used herein, cosmetic preparations can mean care agents. Care agents are understood as meaning care agents for skin and hair. These care agents include, inter alia, cleansing, and restorative action for skin and hair.

In certain embodiments, preparations may be cosmetic and/or dermopharmaceutical preparations, e. g. hair shampoos, hair lotions, foam baths, shower baths, creams, gels, lotions, alcoholic and aqueous/alcoholic solutions, emulsions, wax/fat compositions, stick preparations, powders, or ointments.

Surfactants (or Surface-active substances) that may be present are anionic, non-ionic, cationic and/or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional homologous distribution, but preferably have a narrowed homologous distribution. Typical examples of cationic surfactants are quaternary ammonium compounds, e.g. dimethyl distearyl ammonium chloride, and ester quats, in particular quaternized fatty acid trial-kanolamine ester salts. Typical examples of amphoteric or zwitterionic surfactants are alkyl betaines, alkyl amido betaines, amino propionates, amino glycinates, imidazo-linium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglu-cosides, fatty acid glucamides, alkyl amido betaines, and/or protein fatty acid condensates, the latter preferably based on wheat proteins.

Suitable oily bodies are, for example, alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isoste-aryl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl eru-cate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimer diol or trimer triol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarbox-ylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methi-cone types, inter alia) and/or aliphatic or naphthenic hydro-carbons, for example squalene or dialkyl cyclohexanes.

Suitable emulsifiers are, for example, non-ionogenic sur-factants from at least one of the following groups: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglyco-sides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), polyethylene glycol (molecular weight 400 to 5000), trimethylolpropane, pentaerythritol, sugar alcohols (e.g. sorbitol), alkyl gluco-sides (e.g. methyl glucoside, butyl glucoside, lauryl gluco-side), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof, wool wax alcohols; polysi-loxane-polyalkyl-polyether copolymers and corresponding derivatives; block copolymers, e.g. polyethylene glycol-30 dipolyhydroxystearates; polyalkylene glycols and glycerol carbonate.

The addition products of ethylene oxide and/or of pro-pylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known as refatting agents for cosmetic preparations.

Alkyl and/or alkenyl oligoglycosides can be prepared by reacting glucose or oligosaccharides with primary alcohols having 8 to 18 carbon atoms. With regard to the glycoside radical, both monoglycosides, in which a cyclic sugar radi-cal is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglycer-ide, ricinoleic acid monoglyceride, ricinoleic acid diglyceride, linoleic acid monoglyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid mono-glyceride, malic acid diglyceride, and the technical-grade mixtures thereof which may also comprise small amounts of triglyceride as a minor product of the preparation process. Likewise, suitable are addition products of 1 to 30 mol, preferably 5 to 10 mol, of ethylene oxide onto said partial glycerides.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyl dimethyl ammonium glycinate, N-acylaminopropyl-N,N-dimethylammonium glycinates, for example cocoacyl-amino-propyldimethylammonium glycinate, and 2-alkyl-3-carboxymethyl-3-hydroxyethylimidazolines having in each case 8 to 18 carbon atoms in the alkyl or acyl group, and cocoacylamino-ethylhydroxyethyl-carboxymethyl glycinate. Particular preference is given to the fatty acid amide derivative known under the CTFA name Cocamidopropyl Betaine. Likewise, suitable emulsifiers are ampholytic surfactants. The term "ampholytic surfactants" means those surface-active compounds that, apart from a $C_{8/18}$-alkyl or -acyl group in the molecule, contain at least one free amino group and at least one $CO_2H$ or $SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyl-taurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacyl-aminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, rice germ oil wax, sugarcane wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example hydrogenated jojoba waxes, and synthetic waxes, for example polyalkylene waxes and polyethylene glycol waxes. In addition to the fats, suitable additives are also fat-like substances, such as lecithins and phospholipids.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, hydrophilic silicas, polysaccharides, in particular xanthan gum, agar, alginates, carboxymethylcellulose and hydroxyethylcellulose, and also relatively high molecular weight polyethylene glycol mono- and diesters of fatty acids, polyacrylates, polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethyl-ammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature.

Deodorants and antimicrobial agents that can be used are described in the following text. Cosmetic deodorants counteract, mask, or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichloro-phenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methyl-ethyl)phenol, 2-benzyl-4-chlorophenol, 3-(4-chlorophenoxy)-1,2-propanediol, 3-iodo-2-propynylbutylcarbamate, chlorohexidine, 3,4,4'-trichlorocarbanilide (TTC), antibacterial fragrances, thymol, thyme oil, eugenol, oil of cloves, menthol, mint oil, phenoxyethanol, glycerol monocaprate, glycerol monocaprylate, glycerol monolaurate (GML), diglycerol monocaprate (DMC), salicylic acid N-alkylamides, for example n-octylsalicylamide, or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate. The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or *styrax* or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol, and hydro-carbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, oil of cloves, melissa oil, mint oil, cinnamon leaf oil, linden flower oil, juniper berry oil, vetiver oil, olibanum oil, *galbanum* oil, labdanum oil and lavandin oil. Preference is given to using bergamot oil, dihydro-myrcenol, lilial, lyral, citronellol, phenylethyl alcohol, α-hexylcinnamaldehyde, geraniol, benzylacetone, cyclamen aldehyde, linalool, boisambrene forte, ambroxan, indole, sandelice, lemon oil, mandarin oil, orange oil, allyl amyl glycolate, cyclovertal, lavandin oil, clary sage oil, β-damas-cone, geranium oil bourbon, cyclohexyl salicylate, iraldein gamma, phenylacetic acid, geranyl acetate, benzyl acetate, rose oxide, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, co-emulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohy-drate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-di-chlorophenyl) r-2-(1H-imidazol-1-ylmethyl]-1,3-dioxylan-c-4-ylmethoxyphenyl}piperazine, ketoconazole, elubiol, selenium disulfide, colloidal sulfur, sulfur polyethylene gly-col sorbitan monooleate, sulfur tar distillates, salicyclic acid (or in combination with hexachlorophene), undecylenic acid monoethanolamide sulfosuccinate Na salt, aluminum pyri-thione and magnesium pyrithione/dipyrithione magnesium sulfate.

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are: glycerol; alkylene glycols, for example, ethylene glycol, diethylene glycol, propylene glycol, butylene glycol, hex-ylene glycol, and polyethylene glycols with an average molecular weight of from 100 to 1000 daltons; technical-grade oligo glycerol mixtures with a degree of self-conden-sation of from 1.5 to 10, for example, technical-grade diglycerol mixtures with a diglycerol content of from 40 to 50% by weight; methylol compounds, such as trimethylolethane, trimethylolpropane, trimethylol-butane, pentaerythritol and dipentaerythritol; lower alkyl glucosides, in particular those with 1 to 8 carbon atoms in the alkyl radical, for example methyl and butyl glucoside; sugar alcohols with 5 to 12 carbon atoms, for example sorbitol or mannitol, sugars with 5 to 12 carbon atoms, for example glucose or sucrose; amino sugars, for example glucamine; dialcohol amines, such as diethanolamine or 2-amino-1,3-propanediol.

Suitable preservatives are, for example, phenoxyethanol, formaldehyde solution, pentanediol or sorbic acid.

Medical Device Coatings, Wound Dressings, and Irrigation

In certain embodiments, the disclosure relates to a medical device comprising a coating comprising pentagalloyl glucose optionally in combination with another antibiotic. In certain embodiments, the medical device is an ear tube, eye lenses, contact lenses, coronary stent, metal screw, pin, plate, rod, catheter, artificial knee, cardioverter defibrillator, artificial hip, heart pacemaker, breast implant, spine screws, rods, and discs, intra-uterine devices In certain embodiments, the disclosure relates to a wound dressing comprising pentagalloyl glucose wherein the wound dress comprises an absorbent pad and optionally an adhesive optionally in combination with another antibiotic agent. In certain embodiments, the wound dressing is a foam or compression dressing or a cover dressing such as wraps, gauze and tape.

In certain embodiments, the wound dressing comprises alginate or collagen.

In certain embodiments, the wound dressing a hydrocolloid dressing, e.g., carboxymethylcellulose and gelatin optionally in a polyurethane foam or film, optionally comprising one or more agents selected from, pectin, polysaccharides, and an adhesive.

In certain embodiments, the wound dressing is a hydrogel. Hydrogels are polymers that contain a high content, e.g., greater than 40, 50, 60, 70, 80, 90, or 95%, of hydroxy and/or carboxyl containing monomers or salts thereof, e.g., vinyl alcohol, acrylic acid, 2-hydroxyethylmethacrylate monomers, which can be co-polymers to provide varying degrees of hydration, e.g., copolymerization with ethylene glycol dimethacrylate. Due to the hydrophilic monomers, the hydrogels typically absorb water to contain greater than 70, 80, 85, 90, 95% water by weight. Contemplated hydrogel dressings include: amorphous hydrogel, which are a free-flowing gel that are typically distributed in tubes, foil packets and spray bottles; an impregnated hydrogel, which are typically saturated onto a gauze pad, nonwoven sponge ropes and/or strips; or a sheet hydrogel which are gel held together by a fiber mesh.

In certain embodiments, creams or pre-gel solutions may have an absolute viscosity (cP) of more than 1,000 or 2,000 N s/m$^2$ near room temperature between 20-25 degrees Celsius, for example, pure glycerin typically has a viscosity of about 650 N s/m$^2$ at 20 degrees Celsius.

A flow of wound rinse/irrigation solution is applied across an open wound surface to achieve wound hydration, to remove deeper debris, and to assist with the visual examination. In certain embodiments, the disclosure relates to methods of irrigating using a solution comprising pentagalloyl glucose. In certain embodiments, the disclosure relates to a wound rinse comprising pentagalloyl glucose optionally in combination with normal saline, sterile water, detergent, surfactant, preservatives, or iodine.

In certain embodiments, this disclosure contemplates a kit comprising a container comprising pentagalloyl glucose optionally comprising a second container comprising a solution, normal saline, sterile water, detergent, surfactant, preservatives, iodine, hydrogen peroxide, or sodium hypochlorite or other compounds disclosed herein.

EXAMPLES

Plant Extracts

The leaves of *Schinus terebinthifolia* Raddi (Anacardiaceae) were collected from private property in DeSoto County, Florida. Plant samples were identified and catalogued by Dr. Cassandra Quave at the Emory Herbarium (GEO, Atlanta, Georgia) where voucher specimens were deposited for reference (CQ-651). Fresh plant samples were dried in a dehumidified cabinet. Dried plant material was ground using a grinder and filtered through a 0.5 mm mesh sieve. Powdered plant samples were subjected to two rounds of maceration in 80% aqueous ethanol for 72 h, filtered, and then dried via a rotary evaporator. Crude plant extracts were partitioned using a successive liquid-liquid partitioning scheme. Extraction solvents used: hexanes, ethyl acetate, n-butanol, and water and were labelled B, C, D, and E according to solvent, respectively. Dried crude plant extracts were stored in −20° C. until further use.

Isolation of Bioactive Compounds.

*Schinus terebinthifolia* extract 429 underwent bioassay-guided fractionation. The ethyl acetate partition 429C (13.56 g) was fractionated using a 330 g silica column via normal phase flash chromatography utilizing the following hexane: ethyl acetate gradient: 3 column volumes (CV) 100:0, 30 CV gradient to 0:100, and 32 CV isocratic 0:100. The bioactive fraction 429C-F8 (5.10 g, 37.6% yield), was eluted between 27.5 and 40.0 CV's. Subsequent preparative high-performance liquid chromatography were typically carried out using detecting at 214 nm and 254 nm. The column used for subsequent Prep-HPLC purifications was a reverse phase column. Fraction 429C-F8 was fractionated further via Prep-HPLC using a mobile phase of 0.1% (vol/vol) formic acid in water (A) and 0.1% (vol/vol) formic acid in acetonitrile (B) at a flow rate of 42.5 mL/min. To fractionate 429C-F8, the following gradient (A:B) was used: 0 min (98:2), 3 min (98:2), 11 min (90:10), 38 min (81:19), 58 min (81:19), 58.1 min (80:20), 68 min (80:20), 75.5 min (21:79). The bioactive fraction 429C-F8-PF11 (137.8 mg, 19.7% yield), was eluted between 36.75 and 41.17 min. Fraction 429C-F8-PF11 was fractionated further via Prep-HPLC using a mobile phase of 0.1% (vol/vol) formic acid in water (A) and 0.1% (vol/vol) formic acid in methanol (C) at a flow rate of 42.5 mL/min. To fractionate 429C-F8-PF 11, the following gradient (A:C) was used: 0 min (85:15), 10 min (65:35), 25 min (65:35), 25.1 min (60:40), 35 min (60:40), 35.1 min (2:98), 47 min (2:98). The bioactive fraction 429C-F8-PF11-SF4 (53.6 mg, 36.0% yield), was eluted between 13.0 and 14.0 min.

Bioassay-Guided Isolation of Pentagalloyl Glucose

A natural products library was screened for growth inhibition of CRAB. Lead extracts were then tested in serial dilution and nine extracts from seven species were chosen for further study based on activity. Extract 429, made from the leaves of *Schinus terebinthifolia*, underwent bioassay-guided fractionation for growth inhibition (FIG. 1). Fraction 429C-F8-PF11-SF4 was the most active constituent.

Fraction 429C-F8-PF11-SF4 was identified as a pure substance, pentagalloyl glucose (PGG), IUPAC name [(2R, 3R,4S,5R,6S)-3,4,5,6-tetrakis[(3,4,5-trihydroxybenzoyl) oxy]oxan-2-yl]methyl 3,4,5-trihydroxybenzoate by nuclear magnetic resonance (NMR) spectroscopy and liquid chromatography-Fourier transform mass spectrometry (LC- FTMS). The molecular formula for PGG was assigned as $C_{41}H_{32}O_{26}$ from the (M+) ion peak at 939.1096 m/z. A standard for PGG obtained from a commercial source produced an (M+) ion peak at 939.1094 m/z. Structure identification was accomplished through comparison of $^1H$ and $^{13}C$ NMR spectra to values reported in literature followed by conformation of key connectives using 2D NMR spectroscopic data. The galloyl moieties of PGG produced distinct $^1H$ spectral signals with five singlets that integrated to two protons each between δH 6.88-7.14, a product of the symmetry present in the molecule.

Pentagalloyl Glucose from *Schinus terebinthifolia* Inhibits Growth of Carbapenem-Resistant *Acinetobacter* Baumannii Antibiotic resistance has resulted in multidrug-resistant gram-negative pathogens, such as carbapenem-resistant *Acinetobacter baumannii* (CRAB). CRAB is particularly prominent in healthcare settings among immune-compromised patients and is difficult to manage due to its high capacity for inherent and acquired resistance, including resistance to desiccation. There is currently a lack of new antimicrobials in the drug development pipeline, and many new antimicrobials are specific to gram-positive pathogens. The rise of antibiotic resistance has created a need for new treatments for infections by CRAB and other gram-negative pathogens.

A library of botanical extracts generated from plants was screened for growth inhibition of CRAB. A crude extract of *Schinus terebinthifolia* leaves exhibited 80% inhibition at 256 μg/mL. Bioassay-guided fractionation lead to the isolation of pentagalloyl glucose (PGG), a bioactive gallotannin. PGG inhibited growth of both CRAB and susceptible *A. baumannii* (MIC 64-256 μg/mL), and also exhibited activity against *Pseudomonas aeruginosa* (MIC 16 μg/mL) and *Staphylococcus aureus* (MIC 64 μg/mL). A mammalian cytotoxicity assay with human keratinocytes (HaCaTs) yielded an $IC_{50}$ for PGG of 256 μg/mL. Mechanistic experiments revealed iron chelation as a possible mode of action for the activity of PGG against CRAB. Passaging assays for resistance did not produce any resistant mutants over a period of 21 days. PGG exhibits antimicrobial activity against CRAB. Topical applications of PGG, such as wound rinses and dressings, are contemplated.

Antibacterial Activity of Pentagalloyl Glucose

To determine its activity against a wide range of *A. baumannii* strains, PGG was tested for growth inhibition of one susceptible strain of *A. baumannii* and 23 drug resistant strains (selected for a diversity of resistance profiles, including 19 CRAB strains) (Table 1), yielding minimum inhibitory concentrations (MICs) ranging from 64 to >256 μg/mL (68 to >272 μM) and IC50s ranging from 8 to 64 μg/mL (8.5-68 μM). PGG produced largely similar dose-response curves against 21 of the 24 *A. baumannii* strains tested; much of the variation in MIC values in these 21 strains emerges from small differences in growth inhibition at high concentrations of PGG, since PGG dose-response curves against *A. baumannii* seem to level off around 85-95% inhibition and our definition of MIC is the lowest concentration that exhibits 90% inhibition. PGG was also tested against a panel of other ESKAPE pathogens: *Enterococcus faecium, Staphylococcus aureus, Klebsiella pneumoniae, Pseudomonas aeruginosa*, and *Enterobacter cloacae*. Potent growth inhibition by PGG was observed in *P. aeruginosa, A. baumannii*, and *S. aureus*, with MICs of 16, 64, and 64 μg/mL, respectively (Table 1). The commercially sourced PGG (Sigma-Aldrich) was found to display identical growth inhibition of *A. baumannii* when compared to PGG isolated from *S. terebinthifolia*. Overall, PGG exhibited activity against a wide range of pathogenic bacteria at concentrations ≥64 μg/mL.

TABLE 1

| Growth inhibition of ESKAPE pathogens by pentagalloyl glucose | | | | |
| --- | --- | --- | --- | --- |
| Species | Strain ID | Antibiogram | PGG MIC (μg/mL) | PGG $IC_{50}$ (μg/mL) |
| *Acinetobacter baumannii* | AB5075 | Amk$^R$, Sam$^R$, Fep$^R$, Caz$^R$, Cip$^R$, Gen$^R$, Ipm$^R$, Mem$^R$, Tet$^S$, Tob$^R$ | 256 | 16 |
| *Acinetobacter baumannii* | ATCC17978 | Cst$^S$, Mem$^S$ | >256 | 8 |
| *Acinetobacter baumannii* | Naval-81 | Gen$^I$ | >256 | 16 |
| *Acinetobacter baumannii* | OIFC143 | Antibiogram data not available | 128 | 8 |
| *Acinetobacter baumannii* | NR-9667 | Amk$^R$, Sam$^R$, Fep$^R$, Caz$^R$, Cip$^R$, Gen$^R$, Ipm$^R$, Mem$^R$, Tgc$^R$, Tob$^R$ | 256 | 16 |
| *Acinetobacter baumannii* | AR Bank #0033 | Amk$^S$, Sam$^R$, Fep$^R$, Caz$^R$, Cip$^R$, Cst$^I$, Gen$^R$, Ipm$^R$, Mem$^R$, Tet$^S$, Tgc$^S$, Tob$^R$ | >256 | 8 |
| *Acinetobacter baumannii* | AR Bank #0035 | Amk$^S$, Sam$^R$, Fep$^R$, Caz$^R$, Cip$^R$, Cst$^I$, Gen$^R$, Ipm$^R$, Mem$^R$, Tet$^R$, Tgc$^S$, Tob$^S$ | 256 | 8 |
| *Acinetobacter baumannii* | AR Bank #0036 | Amk$^I$, Sam$^I$, Fep$^R$, Caz$^R$, Cip$^R$, Cst$^I$, Gen$^I$, Ipm$^R$, Mem$^R$, Tet$^R$, Tgc$^I$, Tob$^R$ | >256 | 16 |
| *Acinetobacter baumannii* | AR Bank #0037 | Amk$^S$, Sam$^R$, Fep$^R$, Caz$^R$, Cip$^R$, Cst$^I$, Gen$^R$, Ipm$^R$, Mem$^R$, Tet$^S$, Tgc$^S$, Tob$^R$ | >256 | 8 |
| *Acinetobacter baumannii* | AR Bank #0045 | Amk$^S$, Sam$^R$, Fep$^R$, Caz$^R$, Cip$^R$, Cst$^I$, Gen$^R$, Ipm$^R$, Mem$^R$, Tet$^R$, Tgc$^S$, Tob$^S$ | 128 | 8 |
| *Acinetobacter baumannii* | AR Bank #0070 | Amk$^S$, Sam$^S$, Fep$^S$, Caz$^I$, Cip$^R$, Cst$^I$, Gen$^R$, Ipm$^R$, Mem$^R$, Tet$^S$, Tgc$^S$, Tob$^R$ | >256 | 16 |

27 28

TABLE 1-continued

Growth inhibition of ESKAPE pathogens by pentagalloyl glucose

| Species | Strain ID | Antibiogram | PGG MIC (µg/mL) | PGG IC$_{50}$ (µg/mL) |
|---|---|---|---|---|
| *Acinetobacter baumannii* | AR Bank #0102 | Amk$^R$, Sam$^S$, Fep$^R$, Caz$^R$, Cip$^R$, Cst$^I$, Gen$^R$, Ipm$^S$, Mem$^I$, Tet$^S$, Tsc$^S$, Tob$^R$ | >256 | 8 |
| *Acinetobacter baumannii* | AR Bank #0273 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | 128 | 8 |
| *Acinetobacter baumannii* | AR Bank #0274 | Amk$^S$, Sam$^R$, Fep$^R$, Caz$^R$, Cip$^R$, Cst$^I$, Gen$^R$, Ipm$^R$, Mem$^R$, Tet$^R$, Tgc$^S$, Tob$^S$ | >256 | 64 |
| *Acinetobacter baumannii* | AR Bank #0275 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | >256 | 8 |
| *Acinetobacter baumannii* | AR Bank #0277 | Amk$^S$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | >256 | 8 |
| *Acinetobacter baumannii* | AR Bank #0278 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | >256 | 8 |
| *Acinetobacter baumannii* | AR Bank #0281 | Amk$^S$, Sam$^R$, Fep$^I$, Caz$^R$, Cip$^R$, Cst$^I$, Gen$^R$, Ipm$^R$, Mem$^R$, Tet$^R$, Tgc$^S$, Tob$^S$ | 128 | 8 |
| *Acinetobacter baumannii* | AR Bank #0282 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | >256 | 16 |
| *Acinetobacter baumannii* | AR Bank #0283 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | >256 | 8 |
| *Acinetobacier baumannii* | AR Bank #0284 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | 64 | 8 |
| *Acinetobacter baumannii* | AR Bank #0295 | Amk$^S$, Sam$^R$, Fep$^R$, Caz$^R$, Cip$^R$, Cst$^I$, Gen$^S$, Ipm$^R$, Mem$^R$, Tet$^R$, Tgc$^I$, Tob$^S$ | >256 | 8 |
| *Acinetobacter baumannii* | AR Bank #0299 | Amk$^R$, Sam$^R$, Fep$^R$, Caz$^R$, Cip$^R$, Cst$^I$, Gen$^R$, Ipm$^R$, Mem$^R$, Tet$^R$, Tgc$^S$, Tob$^R$ | 128 | 8 |
| *Acinetobacter baumannii* | AR Bank #0300 | Amk$^R$, Sam$^S$, Fep$^I$, Caz$^R$, Cip$^R$, Cst$^R$, Gen$^R$, Ipm$^S$, Mem$^S$, Tet$^R$, Tgc$^S$, Tob$^R$ | 256 | 8 |
| *Enterococcus faecium* | NR-31915 | Gen$^R$, Van$^R$ | >256 | 128 |
| *Staphylococcus aureus* | LAC | Ery$^S$, Oxa$^R$ | 64 | 16 |
| *Klebsiella pneumoniae* | NR-15410 | Amk$^S$, Sam$^R$, Fep$^R$, Caz$^R$, Cip$^R$, Gen$^S$, Ipm$^R$, Mem$^R$, Tet$^S$, Tob$^S$ | 256 | 8 |
| *Pseudomonas aeruginosa* | PA01 | Antibiogram data not available | 16 | 8 |
| *Pseudomonas aeruginosa* | AR Bank #0054 | Amk$^S$, Fep$^R$, Caz$^R$, Cip$^R$, Gen$^R$, Ipm$^R$, Mem$^R$, Tob$^R$ | >64 | 8 |
| *Pseudomonas aeruginosa* | AR Bank #0064 | Amk$^S$, Fep$^R$, Caz$^R$, Cip$^R$, Gen$^S$, Ipm$^R$, Mem$^R$, Tob$^S$ | 16 | 4 |
| *Pseudomonas aeruginosa* | AR Bank #0090 | Amk$^I$, Fep$^R$, Caz$^R$, Cip$^R$, Gen$^R$, Ipm$^R$, Mem$^R$, Tob$^R$ | >64 | 4 |
| *Pseudomonas aeruginosa* | AR Bank #0092 | Amk$^R$, Fep$^R$, Caz$^R$, Cip$^R$, Gen$^R$, Ipm$^R$, Mem$^R$, Tob$^R$ | >64 | 4 |
| *Pseudomonas aeruginosa* | AR Bank #0094 | Amk$^I$, Fep$^R$, Caz$^R$, Cip$^R$, Gen$^R$, Ipm$^R$, Mem$^R$, Tob$^S$ | 64 | 8 |
| *Pseudomonas aeruginosa* | AR Bank #0095 | Amk$^S$, Fep$^S$, Caz$^S$, Cip$^R$, Gen$^S$, Ipm$^R$, Mem$^R$, Tob$^S$ | 64 | 8 |
| *Pseudomonas aeruginosa* | AR Bank #0100 | Amk$^R$, Fep$^R$, Caz$^R$, Cip$^R$, Gen$^R$, Ipm$^R$, Mem$^R$, Tob$^R$ | >64 | 8 |
| *Pseudomonas aeruginosa* | AR Bank #0103 | Amk$^I$, Fep$^R$, Caz$^R$, Cip$^R$, Gen$^R$, Ipm$^R$, Mem$^R$, Tob$^R$ | 64 | 4 |
| *Pseudomonas aeruginosa* | AR Bank #0105 | Amk$^S$, Fep$^R$, Caz$^R$, Cip$^R$, Gen$^R$, Ipm$^S$, Mem$^R$, Tob$^R$ | >64 | 32 |
| *Pseudomonas aeruginosa* | AR Bank #0108 | Amk$^R$, Fep$^R$, Caz$^R$, Cip$^R$, Gen$^R$, Ipm$^R$, Mem$^R$, Tob$^R$ | >64 | 8 |
| *Pseudomonas aeruginosa* | AR Bank #0110 | Amk$^R$, Fep$^R$, Caz$^R$, Cip$^R$, Gen$^R$, Ipm$^R$, Mem$^R$, Tob$^R$ | 64 | 4 |
| *Pseudomonas aeruginosa* | AR Bank #0111 | Amk$^R$, Fep$^R$, Caz$^R$, Cip$^R$, Gen$^R$, Ipm$^R$, Mem$^R$, Tob$^R$ | 64 | 4 |
| *Enterobacter cloacae* | AR Bank #0032 | Amk$^R$, Sam$^R$, Fep$^R$, Caz$^R$, Cip$^S$, Gen$^R$, Ipm$^R$, Mem$^R$, Tet$^S$, Tob$^I$ | >256 | 64 |

Biofilm Inhibition and Eradication

PGG was tested for biofilm formation inhibition and biofilm eradication against *A. baumannii* AB5075 at concentration gradients of 0.5-64 (sub-MIC) and 2-256 μg/mL, respectively. PGG did not exhibit any antibiofilm activity at the concentrations tested, showing mild promotion of biofilm formation relative to vehicle (DMSO) control at 8-64 μg/mL. However, there was no significant difference between PGG and control with regards to biofilm promotion or inhibition at any concentration tested and no dose-response trend was noted. These data indicate that PGG has no effect on biofilm formation or maintenance at this concentration range.

Cytotoxicity of Pentagalloyl Glucose

Immortalized human keratinocyte cells (HaCaTs) were used in a lactate dehydrogenase (LDH) assay to assess cytotoxicity by PGG and its parents. Both PGG and extract 429 exhibited an $IC_{50}$ of 256 μg/mL Using the median $IC_{50}$ (8 μg/mL) for growth inhibition of *A. baumannii* tested in this study, the therapeutic of index of PGG is 32.

Media Supplementation Experiments

PGG antibacterial activity may be attributed to its chelation of iron. One can use a colorimetric assay to quantify binding of free iron by PGG. One can perform bioassays with iron supplementation and 2,2'-dipyridyl, a known iron chelator, as a control. To elucidate potential mechanisms of action of PGG, *A. baumannii* growth inhibition and time-kill assays were carried out with various supplements in combination with PGG: 0.02% oleic acid, 0.02% polysorbate 80, 1 mM iron (II) sulfate, and 1 mM iron (III) sulfate. In growth inhibition assays of PGG in a gradient of 256-2 μg/mL, oleic acid supplementation produced no change in activity, but polysorbate 80, iron (II) sulfate, and iron (III) sulfate attenuated growth inhibition (Table 2). In time-kill experiments, the CFU/mL curve of PGG alone indicated that PGG's activity at 256 μg/mL is bacteriostatic rather than bactericidal. Furthermore, PGG combined with oleic acid, polysorbate 80, and iron (II) sulfate treatments had roughly tenfold, 100-fold, and 1,000-fold higher CFU/mL measurements, respectively, than PGG alone at the 24 h timepoint.

Restoration Assays

To test for the restoration of bacterial growth after iron addition, iron (II) and iron (III) sulfate were spread at concentrations of 1 mM on PGG-treated *A. baumannii* AB5075 wells that had no visible colonies after 24 h of incubation. Immediately after addition of iron to the agar, all wells containing PGG obtained a purple color, increasing in darkness with increasing PGG concentration. After 24 more hours of incubation, colonies were visible in all of the 0.5×MIC wells, except a single iron (III) supplemented, 0.5×MIC well; another 24 h of incubation resulted in bacterial growth in all wells and darker media showing that *A. baumannii* growth inhibition by PGG can be attenuated by addition of iron.

Resistance Studies

Figure 2C:
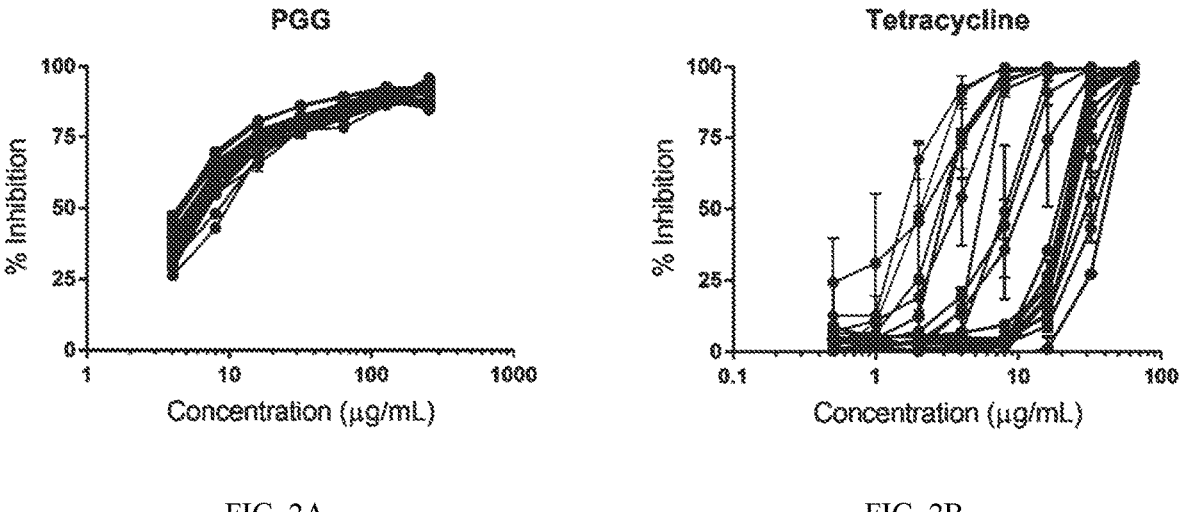
FIG. 2C shows data on the change in MIC of PGG and tetracycline.
Figure 2C:
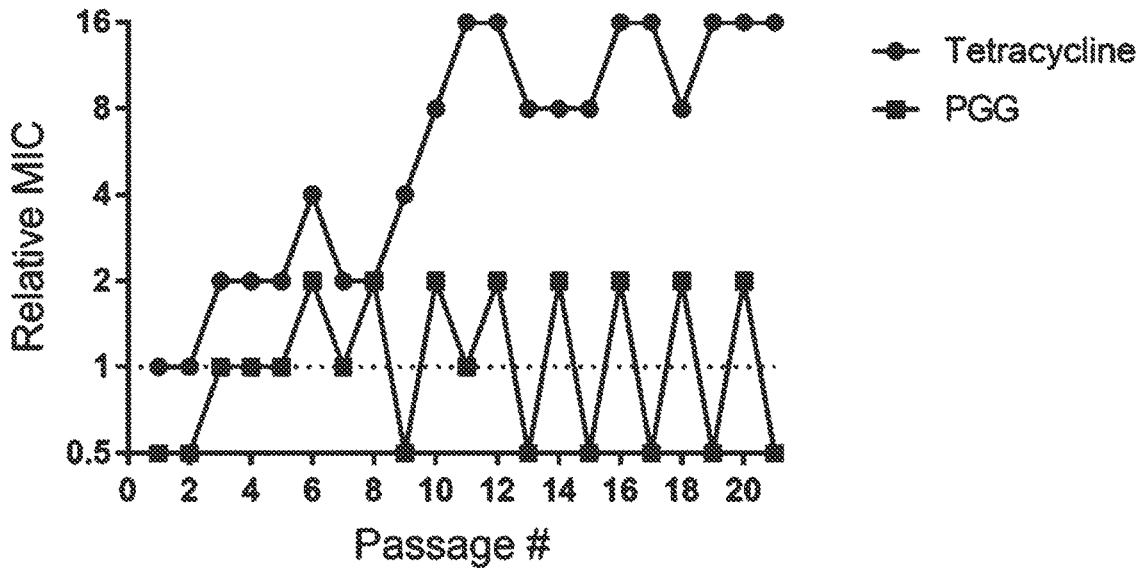
Figure 3A:
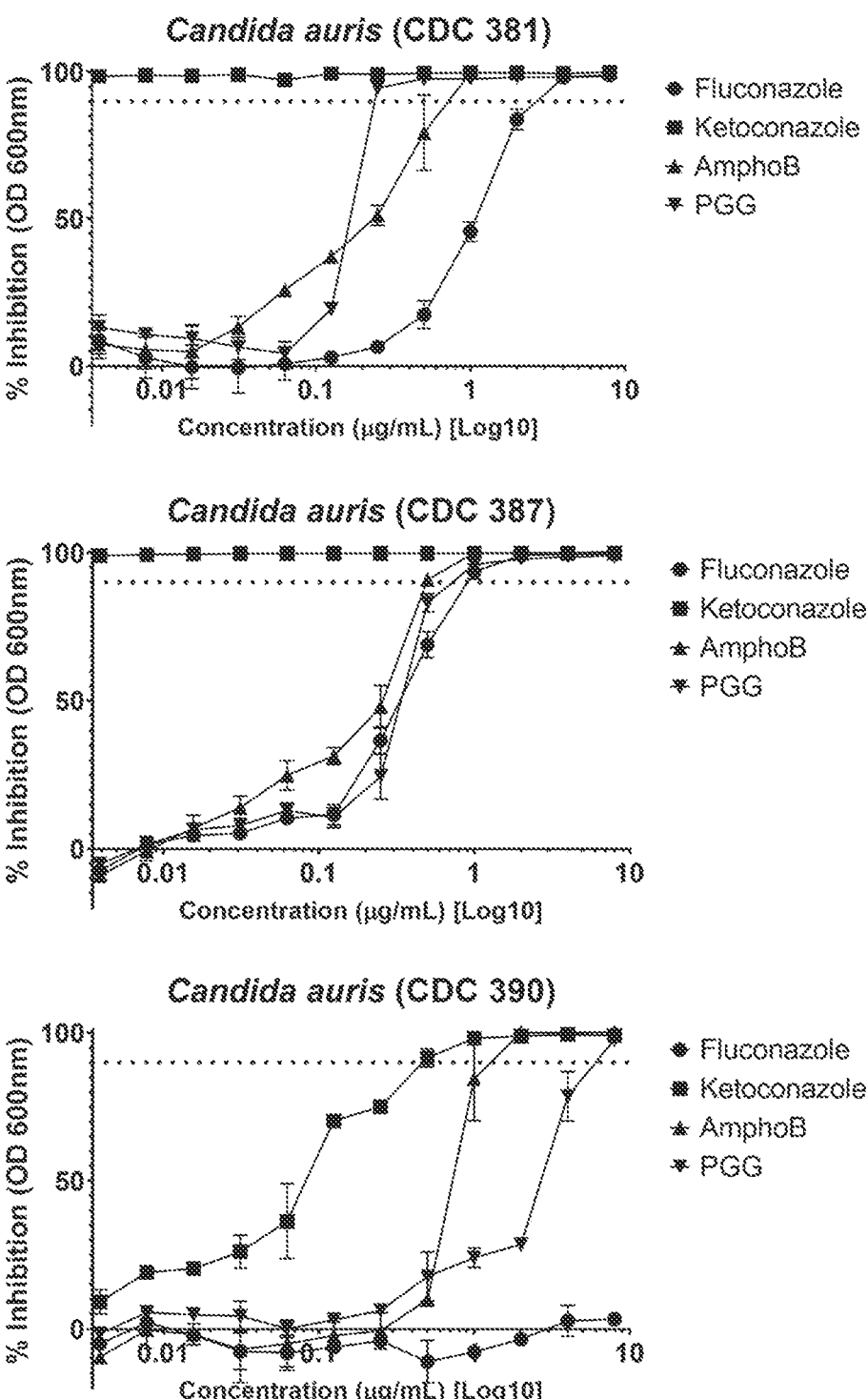
FIG. 3A shows inhibition data comparing PGG and other agents on *Canadida auris* strains.
Figure 3B:
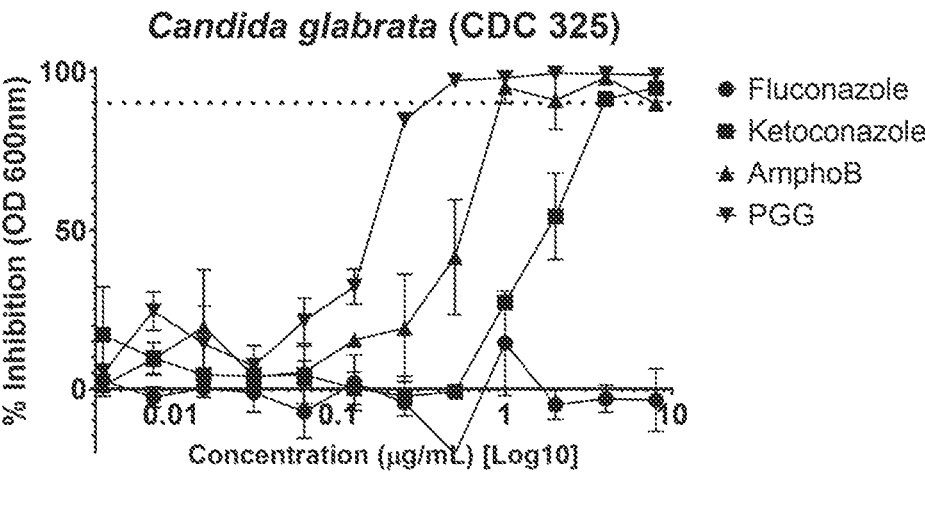
FIG. 3B shows inhibition data comparing PGG and other agents on *Canadida glabrata* strains.
Figure 3B:
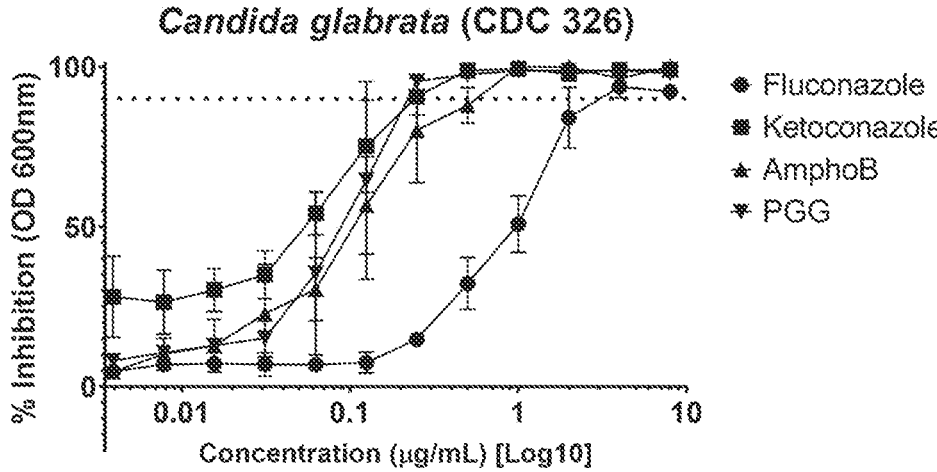
Figure 3B:
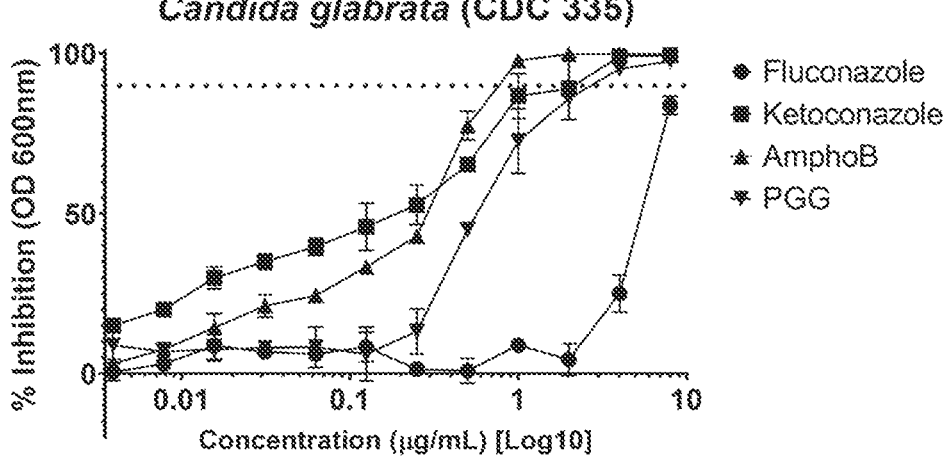
Figure 3C:
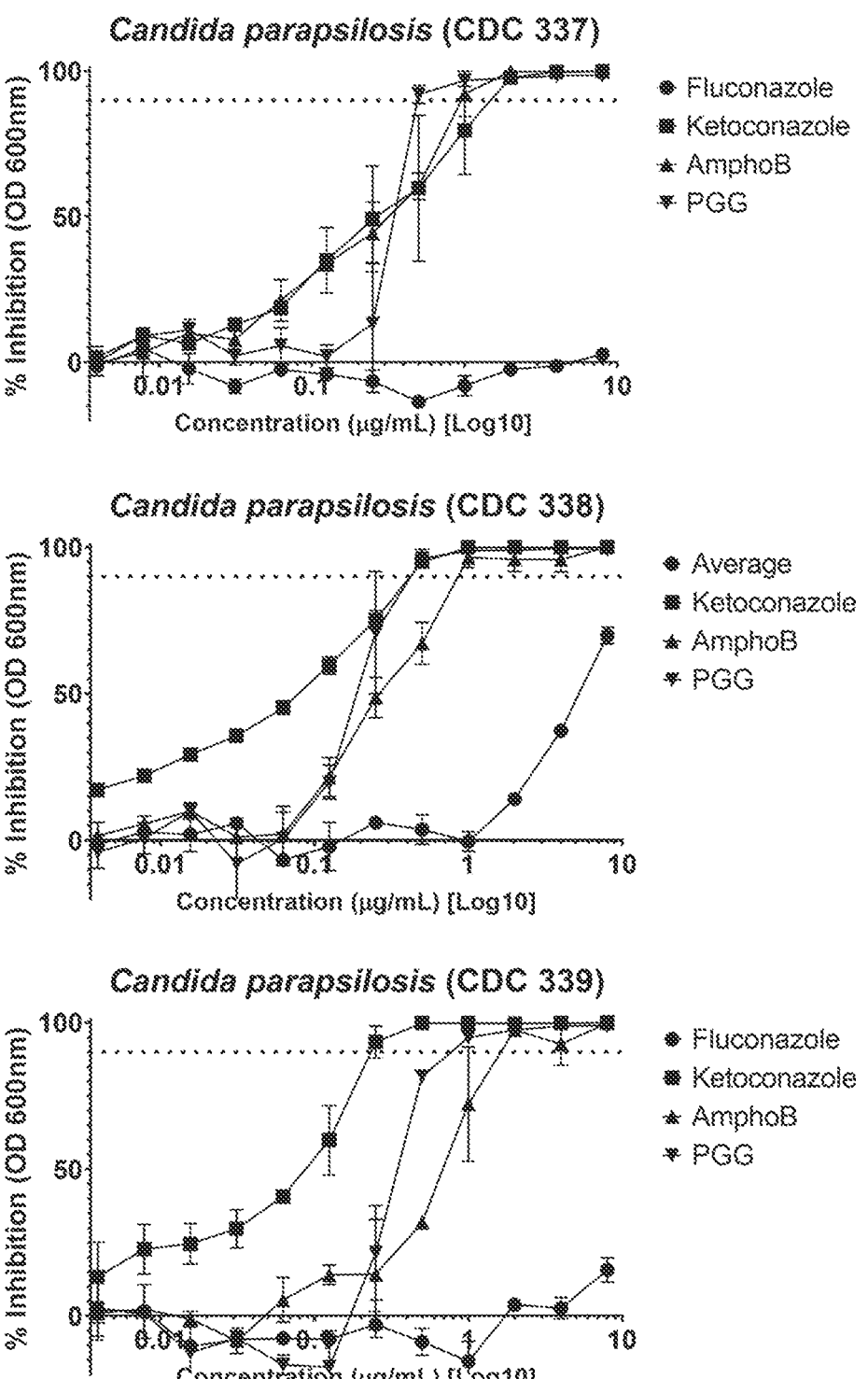
FIG. 3C shows inhibition data comparing PGG and other agents on *Canadida parasilopsis* strains.
Figure 3D:
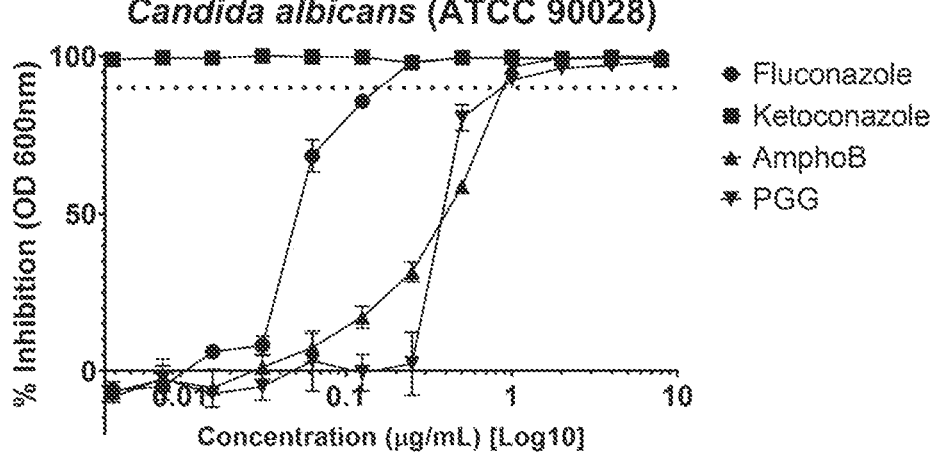
FIG. 3D shows inhibition data comparing PGG and other agents on *Canadida albicans* strains.
Figure 3D:
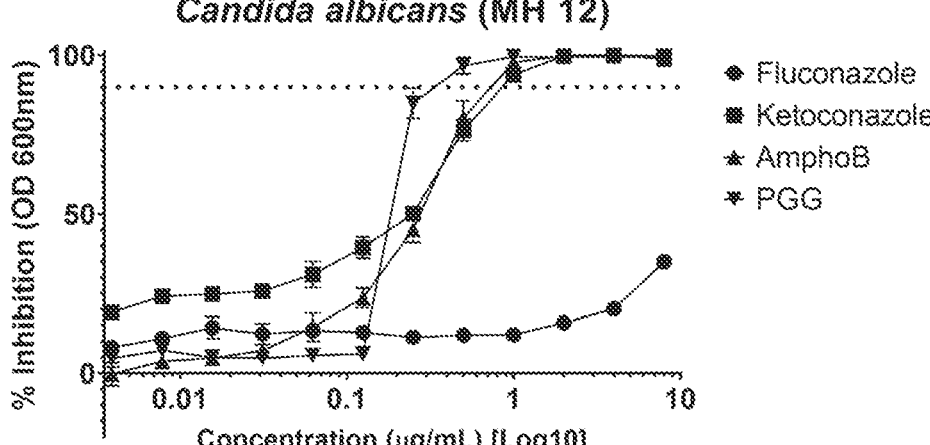

To test for spontaneous development of resistance to PGG, *A. baumannii* AB5075 was inoculated on agar plates containing PGG at 0.5×MIC, 1×MIC, and 2×MIC (128, 256, and 512 g/mL, respectively), and a control plate containing no PGG. After 24 h of incubation, there was a full lawn on the control plate, but no colonies appeared on any of the PGG plates. Next, evolution of resistance was tested by serial passaging *A. baumannii* AB5075 for 21 days in the presence of a PGG gradient, using culture from the 0.5×MIC treatment for each subsequent passage. Serial passaging with a tetracycline gradient served as a control. The MIC of PGG remained stable throughout the 21 daily passages, but the MIC of tetracycline increased from 4 μg/mL (susceptible) to 64 μg/mL (resistant) (FIG. 2C).

PGG Growth Inhibition Mechanism

Experiments with *A. baumannii* indicate supplementation of the growth media with iron (II) sulfate or iron (III) sulfate attenuated growth inhibition by PGG at the concentrations tested. Restoration of *A. baumannii* growth by addition of iron was also related to the concentration of PGG; the higher the concentration of PGG, the less restoration of bacterial growth was observed after iron supplementation, indicating that PGG interacts with iron in a concentration-dependent manner. This concentration-dependent interaction is also evidenced by optical density readings of PGG in iron (II) and iron (III) sulfate supplemented media. This suggests that sequestration capabilities or PGG, and thus *A. baumannii* inhibition, can be overwhelmed by high iron availability in the environment. Applications of PGG as a chelation agent would need to take this into consideration.

Fourteen *A. baumannii* strains tested had MICs>256 μg/mL. The higher MIC values seen amongst many of these resistant strains may be attributed to the ability of *A. baumannii* to grow under iron deficient conditions, such as those generated by the iron chelating compound PGG. Reports indicate that under iron limiting conditions *A. baumannii* strain ATCC 17978 upregulates genes associated with iron acquisition such as the iron-chelating compound acinetobactin and other related siderophores. The higher MIC values (>256 μg/mL) found for many of the *A. baumannii* strains tested, including the reference strain ATCC 17978 which lacks a resistance profile, may be due to these low iron growth adaptations.

Some reports indicate that PGG binds to lipopolysaccharide (LPS), a component of the outer membrane of gram-negative bacteria and a causative agent of sepsis. LPS was previously considered essential to gram negative bacteria, and therefore a target for antibiotics, but some strains, including strains of *A. baumannii*, have been found that can survive without LPS21.

The attenuation of growth inhibition of PGG observed in fatty acid supplementation experiments may be related to binding of PGG with LPS. However, iron supplementation had a larger impact on growth inhibition of *A. baumannii*. Reports indicate that colistin-resistant LPS deficient *A. baumannii* strains may have higher susceptibility to non-polymyxin drugs due to their decreased membrane integrity; however, this has not been observed in clinical isolates, and compensatory mutations likely occur with respect to colistin-resistance. If the mechanism of *A. baumannii* inhibition by PGG is indeed through binding of LPS, these considerations may prove useful for the development of drug delivery systems involving PGG. For example, PGG may be utilized prior to an antibiotic, binding to LPS, in order to first disrupt bacterial membrane integrity.

Anti-Biofilm Activity of PGG

The anti-biofilm activity of PGG against *A. baumannii* contrasts reported anti-biofilm activity against *S. aureus*. However, this discrepancy may be attributed to differences in biofilm mechanisms between *A. baumannii* and *S. aureus*; removal of iron prevents biofilm formation in *S. aureus*, but studies with *A. baumannii* have shown an indifferent response or even increased biofilm formation when iron is limited. Furthermore, previous experiments with deferasirox, a clinical chelator with high affinity to iron, found no significant anti-biofilm activity on *A. baumannii*, suggesting that *A. baumannii* is highly capable of sequestering iron in biofilm. However, every iron chelator has independent activity, and some results have been strain dependent. Also, limiting iron negatively impacts motility, which has been determined to play a key role in virulence.

PGG is capable of chelating iron from the medium to inhibit planktonic growth, but a physical or mechanistic difference in the iron withholding capacity of bacteria interferes with iron chelation capacity of PGG in biofilm. These results also reinforce the concept that differential responses between bacterial species can prevent antibacterial activity in one species from being generalized to other species without specific testing.

Through time-kill assays, PGG was found to be bacteriostatic against *A. baumannii*. Testing PGG against a panel of 24 *A. baumannii* strains with a wide range of resistance profiles showed that activity is generally consistent between strains, and similar growth inhibition activity in a panel of ESKAPE pathogens demonstrated that PGG has activity against both gram-positive and gram-negative bacteria. Passaging *A. baumannii* 21 times in the presence of PGG did not stimulate any spontaneous resistance, in contrast to the same passaging with tetracycline-another bacteriostatic agent-which produced a resistant phenotype (16-fold increase in MIC) after 10 passages. These experiments indicate that PGG has broad-spectrum antibacterial activity, likely inhibiting growth by chelating iron, and that resistance to this activity does not develop quickly in *A. baumannii*.

Cytotoxicity Assays with Human Keratinocytes

In cytotoxicity assays with human keratinocytes, PGG exhibited an $IC_{50}$ of 256 μg/mL, yielding a therapeutic index of 32 for growth inhibition of *A. baumannii*. PGG may therefore be useful as a topical therapy for infections, and the anti-infective traditional use of *S. terebinthifolia* and other members of the Anacardiaceae containing PGG is supported. Pharmacological studies of PGG indicate low oral bioavailability and potential for intravenous administration with possibilities for nanoparticle-based and microbubble-based delivery.

TABLE 2

PGG MIC antifungal agents on *Candida* species

| Species | Strain ID | Antibiogram | MIC (μg/mL) | $IC_{50}$ (μg/mL) |
|---|---|---|---|---|
| *Candida albicans* | ATCC10231 | | 0.5 | 0.25 |
| *Candida albicans* | ARMH12 | Flc$^R$ | 1 | 0.5 |
| *Candida auris* | AR Bank #0381 | Flc$^S$, Vrc$^S$ | 0.5 | 0.25 |
| *Candida auris* | AR Bank #0390 | Flc$^R$, Vrc$^R$ | 0.25 | ND |
| *Candida glabrata* | AR Bank #0325 | Anid$^R$, Casp$^R$, Flc$^R$, Mica$^R$, Vrc$^R$ | 1 | 0.5 |
| *Candida parapsilosis* | AR Bank #0337 | Flc$^R$, Vrc$^R$ | 1 | 0.5 |
| *Candida tropicalis* | AR Bank #0345 | Flc$^R$, Vrc$^R$ | 1 | 0.25 |

Amphotericin B (Amp), anidulafungin (Ani), caspofungin (Cas), itraconazole (Itr), fluconazole (Flu), micafungin (Mic), voriconazole (Vor).

Activity of Pentagalloyl Glucose (PGG) Against Drug Resistant *Candida* Species

The activity of PGG was tested for growth inhibition against two susceptible strains and 6 drug resistant strains from three *Candida* species (Table 2). Minimum inhibitory concentration (MICs) ranged from 0.5 to 8 μg/mL (0.53 μM to 8.5 μM) and $IC_{50}$ values ranging from 0.25 to 2 μg/mL (0.26 μM to 2.1 μM). The activity of PGG followed a dose-response curve against tested strains. Typically the strains tested had MICs less than 2 μg/mL. *Candida glabrata* (AR Bank #0335) yielded the highest MIC at 8 μg/mL.

TABLE 3

PGG MIC antifungal agents on *Candida* species

| Species | Strain ID | Antibiogram | MIC (μg/mL) | $IC_{50}$ (μg/mL) |
|---|---|---|---|---|
| *Candida albicans* | ATCC90028 | Ani$^S$, Cas$^S$, Flu$^S$, Itr$^S$, Vor$^S$, Mic$^S$ | 2.0 | 1.0 |
| *Candida albicans* | MH12 | Ani$^S$, Cas$^S$, Flu$^R$, Itr$^S$, Vor$^R$, Mic$^S$ | 1.0 | 0.5 |
| *Candida parapsilosis* | AR Bank #0337 | Ani$^S$, Cas$^S$, Flu$^R$, Mic$^S$, Vor$^R$ | 1.0 | 1.0 |
| *Candida parapsilosis* | AR Bank #0338 | Ani$^S$, Cas$^S$, Flu$^R$, Mic$^S$ | 1.0 | 0.5 |
| *Candida parapsilosis* | AR Bank #0339 | Ani$^S$, Cas$^S$, Flu$^R$, Mic$^S$ | 2.0 | 1.0 |
| *Candida glabrata* | AR Bank #0325 | Ani$^R$, Cas$^R$, Flu$^R$, Mic$^R$ | 1.0 | 0.5 |
| *Candida glabrata* | AR Bank #0326 | Ani$^S$, Cas$^S$, Mic$^S$, | 0.5 | 0.25 |
| *Candida glabrata* | AR Bank #0335 | Ani$^I$, Cas$^S$, Flu$^R$, Mic$^S$, Vor$^R$ | 8.0 | 2.0 |

The invention claimed is:

1. A method of treating a bacterial infection comprising administering to a subject in need thereof a pharmaceutical formulation comprising an effective amount of pentagalloyl glucose or salt thereof, wherein the pharmaceutical formulation does not comprise hydrogen peroxide, and wherein the bacteria are an *Acinetobacter* species and are resistant to one or more antibiotic agents.

2. The method of claim 1, wherein the bacteria are resistant to one or more antibiotic agents selected from the group consisting of amikacin, ampicillin, sulbactam, cefepime, ceftazidime, ciprofloxacin, erythromycin, colistin, gentamicin, imipenem, oxacillin, tetracycline, tigecycline, tobramycin, vancomycin, and combinations thereof.

3. The method of claim 1, wherein the bacteria are resistant to one or more antibiotic agents selected from the group consisting of ampicillin, sulbactam, cefepime, ceftazidime, ciprofloxacin, gentamicin, imipenem, meropenem, tobramycin, and combinations thereof.

4. The method of claim 1, wherein the bacteria are resistant to a carbapenem antibiotic.

5. The method of claim 4, wherein the carbapenem is selected from the group consisting of imipenem, meropenem, ertapenem, doripenem, panipenem, biapenem, and tebipenem.

6. The method of claim 1, wherein the bacteria are resistant to a penicillin.

7. The method of claim 6, wherein the penicillin is selected from the group consisting of cloxacillin, dicloxacillin, flucloxacillin, methicillin, nafcillin, oxacillin, benzylpenicillin, and phenoxymethylpenicillin.

8. The method of claim 1, wherein the bacteria are *Acinetobacter baumannii* that is resistant to a carbapenem antibiotic.

9. The method of claim 1, wherein administering is contacting the skin, open wound, or wound of the skin of the subject with the pharmaceutical formulation comprising pentagalloyl glucose.

10. A method of treating a fungal infection comprising administering to a subject in need thereof a pharmaceutical formulation comprising an effective amount of pentagalloyl glucose or salt thereof, wherein the pharmaceutical formulation does not comprise hydrogen peroxide, and wherein the fungi are a *Candida* species and are resistant to one or more antibiotic agents.

11. The method of claim 10, wherein the fungi are resistant to one or more antifungal agents selected from the group consisting of anidulafungin, caspofungin, flucona-zole, micafungin, voriconazole, and combinations thereof.

12. The method of claim 9, wherein the pharmaceutical formulation is a lotion, gel or hydrogel.

13. The method of claim 9, further comprising adminis-tering another antibiotic agent.

\* \* \* \* \*